(12) United States Patent
Jevtic et al.

(10) Patent No.: US 10,285,256 B2
(45) Date of Patent: *May 7, 2019

(54) MICROWAVE PLASMA SPECTROMETER USING DIELECTRIC RESONATOR

(71) Applicant: Radom Corporation, West Allis, WI (US)

(72) Inventors: Jovan Jevtic, West Allis, WI (US); Ashok Menon, Shorewood, WI (US); Velibor Pikelja, Milwaukee, WI (US)

(73) Assignee: Radom Corporation, West Allis, WI (US)

(*) Notice: Subject to any disclaimer, the term of this patent is extended or adjusted under 35 U.S.C. 154(b) by 0 days.

This patent is subject to a terminal disclaimer.

(21) Appl. No.: 14/775,497

(22) PCT Filed: Mar. 12, 2014

(86) PCT No.: PCT/US2014/024312
§ 371 (c)(1),
(2) Date: Sep. 11, 2015

(87) PCT Pub. No.: WO2014/159590
PCT Pub. Date: Oct. 2, 2014

(65) Prior Publication Data
US 2016/0025656 A1 Jan. 28, 2016

Related U.S. Application Data

(60) Provisional application No. 61/779,557, filed on Mar. 13, 2013.

(51) Int. Cl.
*G01N 22/00* (2006.01)
*H05H 1/46* (2006.01)
(Continued)

(52) U.S. Cl.
CPC ............... *H05H 1/46* (2013.01); *G01N 22/00* (2013.01); *G21B 1/057* (2013.01); *H01J 37/321* (2013.01);
(Continued)

(58) Field of Classification Search
CPC ............ G01N 22/00; H05H 1/46; H05H 1/24
See application file for complete search history.

(56) References Cited

U.S. PATENT DOCUMENTS 4,765,179 A * 8/1988 Fuller .................... G01N 22/00
73/53.01
5,517,157 A 5/1996 English
(Continued)

FOREIGN PATENT DOCUMENTS

JP H06146026 A 5/1994
JP 2003273615 9/2003
(Continued)

OTHER PUBLICATIONS

Singapore Search Report & Written Opirron of Singapore Application No. 11201507579U.
(Continued)

*Primary Examiner* — Jeff W Natalini
(74) *Attorney, Agent, or Firm* — Boyle Fredrickson, S.C.

(57) ABSTRACT

A dielectric resonator is excited at its natural resonant frequency to produce a highly uniform electric field for the generation of plasma. The plasma may be used as a desolvator, atomizer excitation source and ionization source in an optical spectrometer or a mass spectrometer.

31 Claims, 28 Drawing Sheets

(51) Int. Cl.
*H01J 49/10* (2006.01)
*G21B 1/05* (2006.01)
*H01J 37/32* (2006.01)
*H05H 1/30* (2006.01)
*G01N 21/71* (2006.01)
*H01S 3/0975* (2006.01)

(52) U.S. Cl.
CPC .... *H01J 37/3244* (2013.01); *H01J 37/32467* (2013.01); *H01J 49/10* (2013.01); *H05H 1/30* (2013.01); *G01N 21/718* (2013.01); *H01J 49/105* (2013.01); *H01J 2237/002* (2013.01); *H01S 3/0975* (2013.01); *H05H 2001/4652* (2013.01); *H05H 2001/4682* (2013.01)

(56) References Cited

U.S. PATENT DOCUMENTS

| | | | |
|---|---|---|---|
| 5,942,855 A * | 8/1999 | Hopwood | H01J 37/321 118/723 I |
| 6,265,717 B1 | 7/2001 | Sakata et al. | |
| 2003/0008327 A1 * | 1/2003 | Ornatskaia | C12N 9/12 435/7.1 |
| 2003/0086840 A1 | 5/2003 | Himori et al. | |
| 2003/0160956 A1 | 8/2003 | Chevalier | |
| 2004/0164682 A1 | 8/2004 | Hopwood et al. | |
| 2006/0137613 A1 | 6/2006 | Kasai | |
| 2006/0197529 A1 | 9/2006 | Geifman et al. | |
| 2007/0075051 A1 | 4/2007 | Morrisroe | |
| 2007/0229808 A1 | 10/2007 | Kondo | |
| 2007/0229819 A1 | 10/2007 | Seaward et al. | |
| 2009/0045749 A1 | 2/2009 | Gariachev et al. | |
| 2009/0230962 A1 * | 9/2009 | White | G01N 24/08 324/317 |
| 2010/0320379 A1 * | 12/2010 | Morrisroe | F23C 99/003 250/288 |
| 2011/0000780 A1 | 1/2011 | Tian et al. | |
| 2011/0079505 A1 | 4/2011 | White et al. | |

FOREIGN PATENT DOCUMENTS

| | | |
|---|---|---|
| JP | 2004349199 A | 12/2004 |
| JP | 2005251546 A | 9/2005 |
| JP | 200E185923 A | 7/2006 |
| JP | 2009272127 A | 11/2009 |
| JP | 2011232106 A | 11/2011 |
| JP | 2012104424 A | 5/2012 |
| KR | 1020090112360 A | 10/2009 |
| WO | 03096769 A1 | 11/2003 |

OTHER PUBLICATIONS

EP Supplementary Search Report of Application No. 14772720.0 dated Aug. 24, 2016.
EP Supplementary Search Report of Application No. 14776018.5 dated Aug. 24. 2016.
Singapore Search Report & Written Opinion of Singapore Application No. 1120150780U.
The ISR & Written Opinion from PCT/US2014/024306; Filed: Mar. 12, 2014.
The ISR & Written Opinion from PCT/US2014/024312; Filed: Mar. 13, 2014.

* cited by examiner

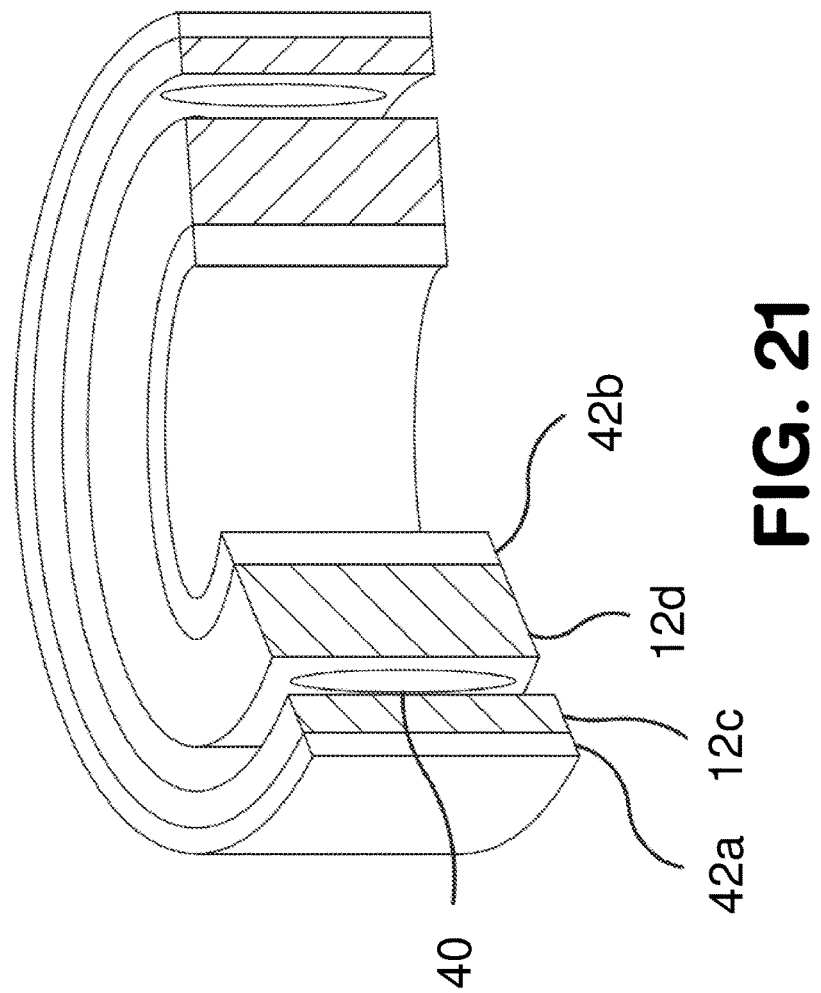

MICROWAVE PLASMA SPECTROMETER USING DIELECTRIC RESONATOR

CROSS-REFERENCE TO RELATED APPLICATIONS

This application claims the benefit of U.S. provisional application 61/779,557 filed 13 Mar. 2013 and hereby incorporated by reference.

FIELD OF THE INVENTION

The present invention relates generally to electrical antennas and in particular to an antenna generating an efficient and uniform electromagnetic field for plasma generation and the like. The present invention is particularly directed to the generation of plasma into which is introduced a substance to be analysed, the plasma causing atomization, excitation and ionization of the substance so that the light it then emits or absorbs, or the ions produced, may be analysed to determine properties of the substance.

BACKGROUND TO THE INVENTION

Plasma sources are used for the generation of gaseous plasma whose unique physical, chemical, optical, thermal, and biological effects are extensively used in broad areas of science and industry. High-frequency plasma sources utilize radio-frequency or microwave electrical energy to sustain a plasma. High-frequency plasma sources typically include a radio-frequency (RF) shield in order to minimize human exposure to high intensity non-ionizing radiation and reduce electromagnetic interference and power losses due to the radiation of electromagnetic energy. Although plasma is typically produced inside an RF shielded enclosure, the beneficial effects of plasma may be realized either inside or outside the radio-frequency shield.

Plasma sources which use radio-frequency or microwave energy to sustain plasma are usually classified as belonging to one of two broad categories, capacitively coupled or inductively coupled. A capacitively coupled plasma source relies on electrical charges stored on capacitor plates to produce an electric field which accelerates the electrons and ions in the plasma. On the other hand, an inductively coupled plasma source relies on a changing magnetic field, produced by the current flowing through a coil, to induce an electric field in the plasma as described by the Faraday's law of induction. Both capacitively and inductively coupled plasma sources find extensive application in the processing of semiconductor wafers. While the capacitively coupled sources are suitable for producing a uniform low-pressure plasma over a relatively large area inductively coupled sources are capable of producing higher density plasma within a smaller volume. In addition, inductive sources are more efficient in coupling large amounts of electrical power into highly electrically conductive plasma, such as in atmospheric plasma torches which generate very high temperature plasma at atmospheric pressure with many applications in science and industry. The present invention relates to inductively coupled plasma sources. High frequency electrical fields for the generation of plasma may make use of a conductive coil ("field applicator") driven by an AC current oscillating in the Megahertz to GigaHertz range. A gas within the coil receives energy from the coil through inductive coupling exciting the gas into a plasma state.

Such inductive coupling techniques for generating plasma have a number of significant problems. First, normally the conductive coil must have multiple "turns" and each turn exhibits a mutual capacitance with adjacent turns of the loop creating field (and hence plasma) inhomogenieties which may be manifested as nonuniform plasma ion speeds, trajectories and densities.

Nonuniformities in the plasma may adversely affect applications in which a uniform plasma is required (for example, for etching in the integrated circuit industry) and may waste energy on undesired plasma processes. Since the regions of plasma with higher electron density absorb more power than the regions with lower electron density, the ionization is further enhanced in high density regions and reduced in low density regions, which may lead to instability. The less uniform the electric field, the more likely it is that the plasma will exhibit instabilities ranging from a departure from a local thermodynamic equilibrium to a contraction into a filamentary discharge. Furthermore, a disproportional energy absorption by the plasma in the regions of high field intensity, which are usually located close to the antenna, limits the energy available to other regions of the plasma. The mutual capacitance also limits the voltage that may be applied to the conductive coil without dielectric breakdown between the turns of the coil.

Second, the large amount of electrical power and hence large amounts of electrical current required to pass through the conductive coil produce significant resistive heating requiring complicated or bulky cooling structures. The use of highly conductive materials, such as copper, can reduce resistive losses, but the use of copper and similar metals is complicated by the susceptibility of such highly conductive materials to corrosion and melting in the harsh environment of the plasma.

Third, efficient driving of the conductive loop requires that the loop be part of a resonant structure implemented by placing a tuning capacitor into the coil circuit.

Capacitors suitable for this purpose are expensive and bulky, and the tuning capacitor may require automated control in order to match the differing load when firstly igniting the plasma and then after stable plasma has been formed, adding further cost and complexity.

SUMMARY OF THE INVENTION

In first embodiment the present invention provides an optical emission spectrometer or as mass spectrometer comprising a plasma generator, the plasma generator comprising a dielectric resonator structure having a central axis and a radiofrequency power source electrically coupled to the dielectric resonator structure to promote an alternating polarization current flow at a natural resonant frequency of the dielectric resonator structure about the axis to generate plasma in an adjacent gas.

A further embodiment the present invention provides a method of analyzing a substance comprising the steps of generating plasma using a plasma generator including a dielectric resonator structure and a radiofrequency power source electrically coupled to the dielectric resonator structure to promote an alternating polarization current flow at a natural resonant frequency of the dielectric resonator structure about the axis to generate plasma in an adjacent gas; introducing a gas into a region adjacent to the dielectric resonator structure; exciting the dielectric resonator structure at a natural resonant frequency to generate plasma in the introduced gas; introducing substance to be analyzed into the plasma; dispersing light emitted by the substance according to the wavelengths of the light or separating ions of the substance created by the plasma according to they mass to charge ratio, detecting either light emitted by the substance according to the wavelengths of the light or ions of the substance created by the plasma according to their mass to charge ratio; and determining the elemental composition of the substance either from the wavelengths of light detected or from the mass to charge ratio of the ions detected.

The radiofrequency power source is preferably electromagnetically coupled to the dielectric resonator structure. The dielectric resonator structure is preferably electrically coupled to the plasma substantially only by induction, there being negligible capacitive coupling.

Preferably the dielectric resonator has a quality factor greater than 100. Preferably the dielectric resonator has electrical resistivity greater than $1 \times 10^{10}$ Ω·cm. Preferably the dielectric resonator has a melting point greater than a melting point of copper. Preferably the dielectric resonator has a loss tangent of less than 0.01. Preferably the dielectric resonator has a dielectric constant greater than five. Preferably the dielectric resonator is selected from the group consisting of alumina ($Al_2O_3$) and calcium titanate ($CaTiO_3$). Preferably the dielectric resonator is a ring or cylindrical annulus having a central opening along the axis. Preferably the ring or cylindrical annulus has a central opening which is circular and has a diameter of between 15 mm and 25 mm.

Preferably the adjacent, gas comprises nitrogen or air.

Preferably the radiofrequency power source provides between 0.5 and 2 kW of power which is able to be coupled into the plasma. Preferably the radiofrequency power source is driven at a frequency which is within two full width at half maximum (FWHM) bandwidths of the resonant frequency of the dielectric resonator structure when the resonator is loaded. Preferably the radiofrequency power source automatically seeks the natural resonant frequency of the dielectric resonator structure to output radiofrequency power at or substantially at the natural resonant frequency of the dielectric resonator structure.

The present invention provides an antenna structure for generating plasma by using a dielectric antenna. The present inventors have determined that such antennas when fabricated with the material having high dielectric constant and low dielectric losses can be operated at resonance to provide for high field strengths with low power dissipation.

While the inventors do not wish to be bound by a particular theory, it is understood that the invention replaces the "conduction" current of electrons in a conventional coil with a "polarization" current of electrons in the dielectric material. The polarization current is due to the minor displacement of elementary charges bound to molecules of the dielectric material under the influence of an electric field. Both types of current (conduction current and polarization current) produce a magnetic field and an induced electric field according to the same laws of electromagnetism. However, since the dielectric material is at once its own capacitor and an inductor, the electric-potential is exactly zero everywhere inside the dielectric and in the space around the dielectric.

As there are neither free nor bound charges, at a macroscopic level the electric potential is exactly zero within and around the dielectric, and the electric field is produced purely by induction, due to the rate of change of the magnetic vector potential in accordance with equation (1):

$$\vec{E} = -\nabla V - \frac{\partial \vec{A}}{\partial t} \quad (1)$$

where $\vec{E}$—vector of electric field strength $\nabla$—gradient operator

V—electric scalar potential (or simply electric potential, potential, or voltage)

$\vec{A}$—magnetic vector potential (or simply vector potential).

Equation (1) may be found in standard texts on electromagnetism, such as equation 6.31 on page 179 of "Classical Electrodynamics" by J. D. Jackson, John Willey & Sons, 1962.

The $\nabla V$ component of the electric field is sometimes referred to as the electrostatic component and the $\partial \vec{A}/\partial t$ component is sometimes referred to as the induced component.

The second term in the right hand side of equation (1) is due to the Faraday's law of induction and may exist even when V=0 everywhere. In a conventional inductively-coupled-plasma (ICP) coil, $\vec{A} \neq 0$ due to the current flowing through the coil, and V≠0 due to a large voltage difference between the ends of the coil or, rather, due to the electrical charges stored on the surface of the coil. However, in an axially symmetric dielectric resonator as used in the present invention, $\vec{A} \neq 0$ due to the polarization current, but V=0 because there are neither free nor bound charges.

Parasitic capacitive coupling is therefore entirely eliminated and the electric field is produced solely by induction. It is further believed that improved current distribution is obtained through lack of "skin" effects in the dielectric material that cause conductive current flow, unlike polarization current, to concentrate in the outermost portions of a ring structure. The polarization current density is nearly uniform across the cross section of the dielectric in much the same way that an electric field is uniformly distributed across the cross-section of dielectric in a capacitor. The skin effect or the rapid attenuation of electromagnetic waves as they penetrate into a conducting material is effectively absent in low-loss dielectric materials.

The elimination of capacitive coupling is a considerable advantage over ICP sources which suffer particularly large capacitive coupling due to their use of a multi-turn coil. A conventional method of reducing the parasitic capacitive coupling is to interpose an electrostatic or Faraday shield between the coil and the plasma. Since a solid conductive sheet would block both the inductive and the capacitive components of the electric field, the electrostatic shield usually has a series of narrow slots normal to the direction of the current in the coil. A disadvantage of an electrostatic shield is that it reduces the inductive coupling between the coil and the plasma, for several reasons: a) the coil must be placed further away from the plasma in order to accommodate the electrostatic shield, b) screening currents, opposite of the antenna current, flow along the portion of the shield which does not have slots, c) the vicinity of the shield to the coil adds significant capacitive loading which increases the current and Ohmic losses in the coil. In addition, the small spacing between conductors limits the maximum power due to the reduced breakdown voltage. Finally, the deviation of the electric field from an ideal inductive field is the largest in the vicinity of the slots where the coupling to the plasma is most significant.

In addition to parasitic capacitive coupling and the limitations imposed by the electrostatic shields, the conventional inductively plasma sources suffer from the following limitations:

a) Large currents in coil conductors dissipate significant amount of heat which must be removed by fluid cooling, requiring a fluid manifold and a chiller. Use of dielectric cooling fluids which are damaging to the environment is not uncommon in semiconductor applications. Added complexity, size, and cost of the cooling system make the conventional inductively coupled plasma sources unsuitable for design scaling, portable applications, and designs where space available for the plasma source is limited.

b) The corrosion which builds on the surface of the coil over a period of time greatly increases Ohmic losses in the coil and may necessitate a coil replacement.

c) Coils made of metal, such as Copper, melt at relatively low temperature, are degraded by plasma sputtering, and are incompatible with ultra-high-vacuum processes. Therefore, in low-pressure plasma applications, the coil must be separated from the plasma by the walls of the vacuum chamber and in atmospheric pressure plasma applications, the coil must be located at a sufficient distance from the plasma. This reduces the inductive coupling between the coil and the plasma and complicates the mechanical construction of the plasma source.

d) The difference of electric-potential between the turns of the coil and the coil and the shield may cause a dielectric breakdown, limiting the maximum power that can be processed.

e) The inductance of the coil must be resonated with a tuning capacitor, typically a bulky and expensive variable vacuum capacitor forming a part of an external impedance matching network, adding to the size, cost, and complexity of the plasma source, while further limiting the maximum power that can be processed and reducing the efficiency due to the losses in the impedance matching network.

The present invention advantageously avoids all these problems, providing improved plasma uniformity, better control of ion speeds and trajectories, reduced deposition or sputtering of the walls of any plasma chamber, better efficiency in coupling electrical energy into useful plasma processes, higher limits to the power that can be coupled into useful plasma processes and complete elimination of the electrostatic or Faraday shield.

Specifically then, the present invention provides a plasma generator having a dielectric resonator structure having a central axis and a radiofrequency power source electrically coupled to the dielectric resonator structure to promote an alternating polarization current flow at a natural resonant frequency of the dielectric resonator structure about the axis to generate plasma in an adjacent gas. The radiofrequency power source is electrically coupled to the dielectric resonator. As a magnetic field is also present, the radiofrequency power source is both electrically coupled and magnetically coupled to dielectric resonator structure; hence the radiofrequency power source may be said to be electromagnetically coupled to the dielectric resonator structure. The coupling promotes an alternating polarization current flow at a natural resonant frequency of the dielectric resonator structure. The radiofrequency power source is driven at a frequency or a range of frequencies (such as broadband) which is sufficient to couple at least some power into the dielectric resonator structure at its natural resonant frequency. Preferably the radiofrequency power source is driven at a frequency which is related to the natural resonant frequency of the dielectric resonator structure. More preferably the radiofrequency power source is driven at a frequency which is within two full width at half maximum (FWHM) bandwidths of the resonant frequency of the dielectric resonator structure when the resonator is loaded.

The bandwidth of an unloaded dielectric resonator is very narrow and may broaden by a factor of 100 when loaded with the plasma.

It is thus a feature of at least one embodiment of the invention to provide an improved radiofrequency antenna for the generation of intense but uniform electrical fields for plasma production.

The dielectric resonator may have any one r more of the qualities of a quality factor of greater than 100, an electrical resistivity greater than $1 \times 10^{10}$ Ω·cm, a dielectric constant with a loss tangent of less than 0.01, and a dielectric constant greater than five.

It is thus a feature of at least one embodiment of the invention to provide a dielectric material that produces extremely low losses at radiofrequency fields and high power levels to minimize problems of cooling and energy loss.

The dielectric resonator may be of a material having melting point greater than a melting point of copper.

It is thus a feature of at least one embodiment of the invention to provide a material that is robust against the extremely high temperatures of plasma.

The dielectric material may, for example, be alumina (Al2O3) or calcium titanate (CaTiO3).

It is thus a feature of at least one embodiment of the invention to provide an apparatus that may be constructed of relatively common and manufacturable materials.

The dielectric resonator may be a ring having a central opening along the axis.

It is thus a feature of at least one embodiment of the invention to provide a dielectric resonator that is relatively simple to manufacture.

The ring may have a central opening of at least one millimeter diameter or at least one half inch. The ring may have a central opening which differs according to the area of application of use of the dielectric resonator. The central opening may be circular in it may be any other shape convenient to the application. Preferably the central opening is circular. Where the central opening is circular it will have a characteristic dimension which is its diameter. Where the central opening is not circular the size of the central opening will have one or more characteristic dimensions which are representative of widths across the opening. For use in the fields of optical spectroscopy and mass spectrometry the central opening may have a characteristic dimension between 1 mm and 50 mm. For use in the field of lasers the central opening may have a characteristic dimension between 1 mm and 1 m. For use in the fields of electron cyclotron resonance plasma sources the central opening may have a characteristic dimension between 10 mm and 500 mm. For use in the field of semiconductor processing the central opening may have a characteristic dimension between 10 mm and 1 m. For use in the fields of material processing and propulsion the central opening may have a characteristic dimension between 1 mm and 1 m. For use in the field of ICR heating the central opening may have a characteristic dimension between 1 m and 20 m.

Preferably, for use in the fields of optical spectroscopy and mass spectrometry the central opening is circular and has a diameter of between 1 mm and 50 mm, more preferably between 5 mm and 30 mm, more preferably still between 1.5 mm and 25 mm.

The dielectric resonator may take the form of a cylindrical annulus, having a central opening concentric with the outer diameter of the annulus. However other shapes of dielectric resonator are contemplated. Preferably the dielectric resonator takes the form of a cylindrical annulus, having a central opening concentric with the outer diameter of the cylindrical annulus.

It is thus a feature of at least one embodiment of the invention to provide a dielectric resonator that is readily adaptable to forming plasma in flowing gas.

To that end, the plasma generator may include a gas port introducing gas into the ring along an axis of the ring.

It is thus a feature of at least one embodiment of the invention to provide the elements of a plasma torch for spectroscopic or other applications.

The radiofrequency power source may automatically seek the natural resonant frequency of the dielectric resonator structure to output radiofrequency power at the natural resonant frequency of the dielectric resonator structure. This may be readily achieved by creating a phase lock between the amplifier signal and the wave reflected from the resonator using a directional coupler as a detector.

It is thus a feature of at least one embodiment of the invention to provide a plasma generator that may automatically adjust to variations in the dielectric resonant material or its environment. Such variations include changes caused by altered plasma conditions, such as the change of plasma gas, pressure, sample type (aqueous or organic), and gas and sample flow rates when the invention is applied to the fields of optical spectroscopy and mass spectrometry, for example. In addition, the permittivity of low-loss dielectric materials and the dimensions of external components in the environment of the dielectric oscillator, such as an RF shield, may change with temperature which may affect the tuning in applications which require extreme operating temperatures, such as a microwave rocket nozzle.

Preferably the radiofrequency power source automatically seeks the natural resonant frequency of the dielectric resonator structure to output radiofrequency power at or substantially at the natural resonant frequency of the dielectric resonator structure.

The radiofrequency power source may be a magnetron or a solid-state or vacuum tube oscillator. The radiofrequency power source may comprise one or more of a magnetron, a solid state oscillator or a vacuum tube oscillator.

Preferably the dielectric resonator structure is electrically coupled to the plasma substantially only by induction, there being negligible capacitive coupling.

It is thus a feature of at least one embodiment of the invention to permit the generation of extremely high frequency plasma. The invention may be utilized with radiofrequency power sources operating at least within the range of 1 MHz to 10 GHz, and specifically within the VHF range (30 MHz-300 MHz) and the UHF range (300 MHz-3 GHz).

Plasmas may be sustained in a variety of gases, including but not limited to argon, nitrogen, helium and air. Plasmas may be used in a variety of applications, including high-temperature plasma for plasma cutting, welding melting, and surface treatment of materials, destruction of hazardous materials, vitrification of waste, ignition of hydro-carbon fuels; light emitted by excited atomic and molecular species for optical-emission spectroscopy and light sources; ions for mass-spectroscopy, ion-implantation, and ion-thrusters; small particles for material spheroidization, synthesis of nano-materials and plasma spraying of surface coatings; reactive plasma species for gasification and the production of syngas; supersonic gas flow for scientific and in-space propulsion applications; combination of plasma effects and products for lean internal combustion and exhaust detoxification, plasma assisted combustion, ore reduction and processing, hydro-carbon fuel reforming, air purification and removal of airborne contaminants in research facilities, hospitals etc.

The present invention is particularly directed to the excitation and ionization of substances so that the light they then emit, or the ions produced, may be analysed to determine properties of the substance. Important properties which may be determined include the elemental composition of the substance and the relative quantities of elemental components of the substance. The present invention is especially directed for application within the fields of optical emission spectroscopy (OES) and mass spectrometry (MS), the microwave plasma source replacing, for example, conventional inductively coupled plasma (ICP) sources. Where the plasma is used to excite or ionize a substance so that it may be analysed using spectroscopy or spectrometry, the substance to be analysed is introduced into the plasma. As well as exciting or ionizing the substance to be analysed, the plasma may also atomise the substance and it may desolvate the substance. As an atomization source, the plasma generator of the present invention may be used for atomic absorption (AA) spectroscopy.

The optical emission spectrometer of the present invention preferably comprises an optical sensor, wherein the optical sensor comprises a dispersive element for dispersing light emitted by the plasma according to the wavelength of the light; and an optical detector for detecting the dispersed light. Hence the optical emission spectrometer of the present invention preferably comprises a plasma generator, the plasma generator comprising a radiofrequency power source and a dielectric resonator; a dispersive element for dispersing light emitted by the plasma according to the wavelength of the light; and an optical detector for detecting the dispersed light. Preferably the optical emission spectrometer will further comprise one or more of one or more optical focusing elements which may be lenses or mirrors; mirrors for changing the direction of one or more beams of light; a focal plane array detector comprising multiple detecting elements for simultaneously detecting light dispersed by the dispersive element, the focal plane array detector forming at least part of the optical detector; a controller for controlling the spectrometer; and a controller for receiving an output from the optical detector, which may be the same controller as is used for controlling the spectrometer. In a preferred form, the dispersive element comprises a grating.

The mass spectrometer of the present invention preferably comprises a gas port suitable for delivering sample material into the plasma generated by the plasma generator; a sample cone and a skimmer cone; at least one ion focusing element; a mass analyzing element; and an ion detector for detecting sample material ionized by the plasma. Preferably the mass spectrometer further comprises a controller for controlling the mass spectrometer and a controller for receiving an output from the ion detector.

The particular objects and advantages described may apply to only some embodiments falling within the claims and thus do not define the scope of the invention.

DESCRIPTION OF THE DRAWINGS

FIG. 21 is a perspective partial cutaway view of a dielectric resonator in the form of two coaxial ceramic rings, together with two RF shields.

DETAILED DESCRIPTION

Figure 1:
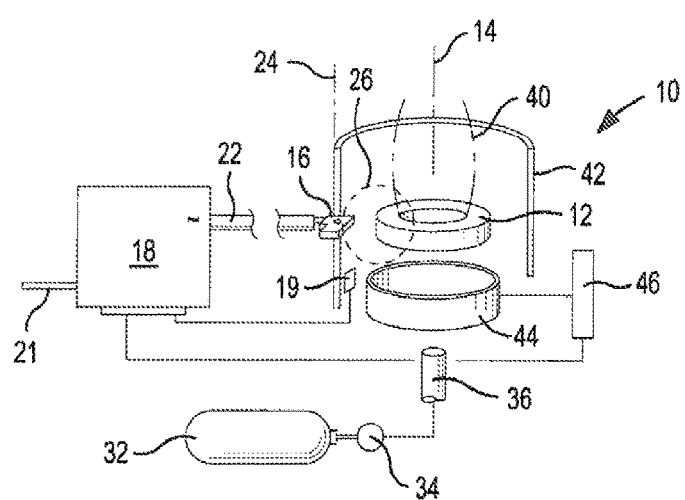
FIG. 1 is a partial cutaway perspective view of a plasma generator using a ring dielectric resonator of one embodiment of the present invention.

Referring now to FIG. 1, a plasma generator 10 of the present invention may provide for a dielectric resonator 12 being in this embodiment a cylindrical annulus centered about an axis 14.

As is understood in the art, dielectric materials are substantially insulators with respect to direct currents (that is when a dielectric is placed in an electric field electrical charges do not flow freely through the material as they do in a conductor) but can provide for polarization currents produced by slight shifts in the equilibrium positions of bound electrons or ions in the material.

In this embodiment, the dielectric resonator 12 may be made of alumina ($Al_2O_3$) and may be a circular annulus or ring being two inches (0.0508 m) in outer diameter, one inch (0.0254 in) in inner diameter and 0.75 inches (0.01905 m) in length along axis 14 and having an electrical resonance frequency at approximately 2.45 GigaHertz. This material exhibits a quality factor of greater than 5000, a relative dielectric constant of 9.8 and retains its electrical properties and physical integrity at temperatures exceeding 1000 degrees centigrade.

An alternative material for the dielectric resonator 12 may be calcium titanate ($CaTiO_3$) being 3.13 inches (0.0795 m) in outer diameter 2.34 inches (0.05944 m) in inner diameter and 1.12 inches (0.02845 m) in length and resonating at approximately 430 MegaHertz. This ring exhibits a quality factor in excess of 5000 and has a relative dielectric constant of 200.

Many types of advanced technical ceramics meet these requirements, but other dielectric materials with similar electrical properties may be used instead.

More generally, the dielectric material of the dielectric resonator 12 may have the following properties: (a) loss tangent less than 0.01, (b) quality factor greater than 100, (c) relative dielectric constant larger than 5. Alternatively the quality factor should be greater than 1000.

Desirably the dielectric material may have a resistivity greater than $1 \times 10^{10}$ Ohm centimeters and typically greater than $1 \times 10^{14}$ Ohm centimeters. Desirably, the dielectric material may have a melting point higher than copper or other comparable conductive metals. The dielectric constant is preferably greater than five and more desirably greater than nine. These examples are not intended to be limiting. Indeed, dielectric resonators comprising materials with resistivity as low as 100 Ohm centimeters may be used and there appears to be no practical upper limit on resistivity. Hence the dielectric resonator preferably has electrical resistivity within one of the following ranges: 100-1000 Ohm centimeters; 1000-10000 Ohm centimeters; $10^4$-$10^5$ Ohm centimeters; $10^5$-$10^6$ Ohm centimeters; $10^6$-$10^7$ Ohm centimeters; $10^7$-$10^8$ Ohm centimeters; $10^8$-$10^9$ Ohm centimeters; $10^9$-$10^{10}$ Ohm centimeters; $10^{10}$-$10^{12}$ Ohm centimeters; $10^{12}$-$10^{14}$ Ohm centimeters; greater than $10^{14}$ Ohm centimeters.

The dielectric constant of the dielectric resonator preferably lies within one of the following ranges: 5-6, 6-7, 7-8, 8-9 or greater than 9.

Preferably the dielectric resonator has a dielectric constant with a loss tangent which lies within one of the following ranges: less than $10^{-4}$; $10^{-4}$-$10^{-3}$; $10^{-3}$-$10^{-2}$.

The resonant frequency of a ring is approximately inversely proportional to the square root of the relative dielectric constant and approximately inversely proportional to the linear size of the ring, if all three dimensions of the ring are changed by the same factor, allowing these examples to be readily modified to other dimensions.

A precise resonant frequency of a given dielectric resonator may be best obtained using computer simulations, such as may be achieved using ANSYS-HFSS electromagnetic field solver, for example. However, a first order estimate can be obtained by using the following approximate formula which neglects the effect of any RF shield:

$$f_0 = \frac{c_0}{\sqrt{2\pi\varepsilon_r ht \left[\ln\left(8R\sqrt{\frac{\pi}{ht}}\right) - 1.75\right]}}, \quad (2)$$

where:

$c_0 = 3 \cdot 10^8$ m/s—speed of light in free-space $\varepsilon_r$—relative permittivity of the dielectric resonator h—length of the dielectric resonator in [m]

t—thickness of the dielectric resonator, i.e., (O.D.−I.D.)/2 in [m]

R—mean radius of the dielectric resonator, i.e., (O.D.+I.D.)/4 in [m]

Use of equation (2) with a dielectric resonator suitable for use in optical spectroscopy or mass spectrometry in which the dielectric comprised a cylindrical annulus of outer diameter 0.0508 m (2"), the resonator having a circular central opening concentric with the outer diameter of the annulus, the central opening having a diameter of 0.0254 m (1"), the dielectric resonator having a thickness (i.e. a cylinder length) of 0.01905 m (0.75"), and $\varepsilon_\gamma = 9.8$, equation (2) provides a resonant frequency of $f_0 = 2.35$ GHz. When tested, the measured resonant frequency was found to be 2.45 GHz, approximately 4% higher than the predicted value. Hence in practical situations equation (2) may be used to predict the resonant frequency with a useful accuracy. The dielectric resonator 12 may be positioned near a coupling antenna 16 in turn attached to a radio frequency power supply 18 the latter producing a high frequency electrical current exciting the coupling antenna 16 at the resonant frequency of the dielectric resonator 12. Matching of the frequency output of the radiofrequency power supply 18 to the resonant frequency of the dielectric resonator 12 may be done manually by adjusting a frequency setting, or automatically, for example, by using a feedback system detecting impedance changes associated with resonance. Automatic tuning may also be provided by "self resonance" using feedback from a sensing antenna 19 whose output drives the radiofrequency power supply 18 acting as an amplifier. Self resonance is provided by ensuring a necessary loop phase shift as is generally understood in the art. By adjusting the phase shift in the loop, such as by changing the length of the cable or by using a phase-shifter, one can create the conditions for oscillations. The loop should contain a signal limiting component, such as a limiter at the input of the amplifier. The radiofrequency power supply 18 receives electrical power 21, for example, line current from a conventional source.

Figure 14:
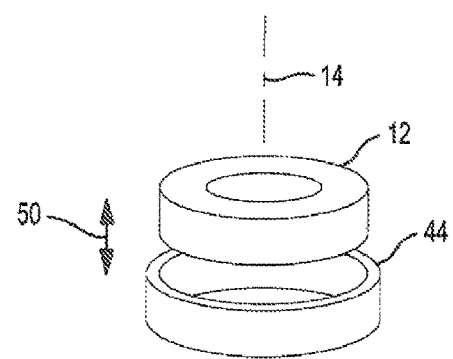
FIG. 14 is a figure similar to FIG. 13 showing alternative tuning structure in which one dielectric resonator may fit over the other dielectric resonator for tuning.

Referring now to FIG. 1 and FIG. 14, the resonant frequency of the dielectric resonator 12 may be adjusted not only by changing the dimensions of the dielectric resonator 12 but by placing a second dielectric tuning element 44 in proximity to the dielectric resonator 12. In this example of FIG. 14, the tuning element 44 is a cylindrical annulus larger than the outer diameter of the dielectric resonator 12 and aligned with axis 14. The tuning element 44 is attached to a mechanism 46 (for example, a rack and pinion lead screw or the like) allowing it to be moved along the axis as indicated by movement arrow 50 to change the inductive coupling between tuning element 44 and dielectric resonator 12 thereby changing the resonant frequency of dielectric resonator 12. Because tuning element 44 may fit around dielectric resonator 12 close coupling may be established for sensitive tuning. The movement of the tuning elements 44 may be manual or automatic according to feedback control, for example, according to sense impedance as described above.

Figure 13:
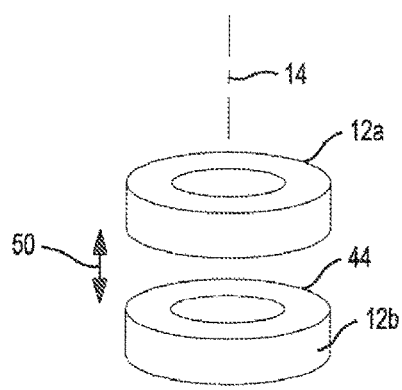
FIG. 13 is a perspective view of two identical ring-shaped dielectric resonators movable with respect to each other for tuning.

Referring now to FIG. 13, in an alternative embodiment, two identical dielectric resonators 12a and 12b may be used with dielectric resonator 12b acting as tuning element 44. The use of two identical components provide greatly increased tuning range and an extended region of uniform electrical field. One or both of the dielectric resonator 12a and dielectric resonator 12b may provide for electrical fields generating plasma, by which it is meant that the desired plasma may be formed inside one of the rings only, or inside both rings, depending upon the gas flow conditions, the geometry of the torch, the location of an ignition source and the selected resonant mode.

Alternatively, in either of the above examples depicted in FIG. 13 and FIG. 14, the tuning elements 44 may be a metal such as aluminum, copper, or silverplated copper to provide similar tuning effects.

The relative position of tuning element 44 with respect to the dielectric ring antenna alters the resonant frequency. The resonant frequency can be expressed as a function of the coupling coefficient k between the dielectric ring and the tuning element 44. Coupling coefficient k is a number between 0 and 1. In the absence of the RF shield, qualitatively, k increases as the tuning element is brought closer to the dielectric ring. The formulas below are for qualitative analysis only a better estimate of the resonant frequency can be obtained by computer simulation of electromagnetic fields, such as by using ANSYS-HFSS software.

The general expression for the resonant frequency of two coupled resonators is given by $$f_{a,b} = \frac{f_1^2 + f_2^2 \pm \sqrt{(f_1^2 - f_2^2)^2 + 4k^2 f_1^2 f_2^2}}{2(1 - k^2)} \quad (3)$$

where:

$f_a, f_b$—resonant frequencies of the parallel and anti-parallel modes k—coupling coefficient (0<k<1)

$f_1$—resonant frequency of the dielectric ring $f_2$—resonant frequency of the tuning element ($f_2 = 0$ if metal)

There are 2 cases of special interest:

1. For a tuning element 44 made of metal, whether the same size as the dielectric ring or not (such as depicted in both FIGS. 13 and 14,) the expression above simplifies to:

$$f = \frac{f_1}{\sqrt{1 - k^2}}.$$

2. For two identical ring, as in FIG. 13, where the rings are both dielectric, there are two possible modes of operation, depending on the operating frequency. In a lower frequency mode, the polarization currents in the two rings flow in the same direction about the axis, i.e., they are parallel or in phase. The frequency of this mode is approximately given by $$f_a = \frac{f_1}{\sqrt{1 + k}}.$$

Alternatively, in the case of a higher frequency mode, the polarization currents in the two rings flow in opposite directions about the axis, i.e., they are anti-parallel or 180 degrees out of phase. The frequency of the second mode is approximately given by $$f_b = \frac{f_1}{\sqrt{1-k}}.$$

The two frequency modes have different field distributions. The lower frequency mode is the strongest in the space between the rings, while the higher frequency mode is strongest inside the rings and zero at the mid-point between the rings.

Figure 2:
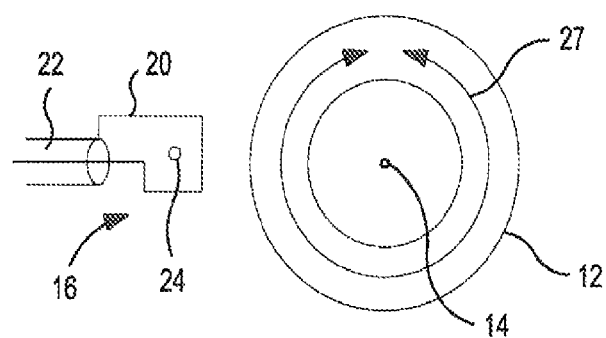
FIG. 2 is a top plan view of the ring dielectric resonator of FIG. 1 showing the orientation of polarization current flow.
Figure 11:
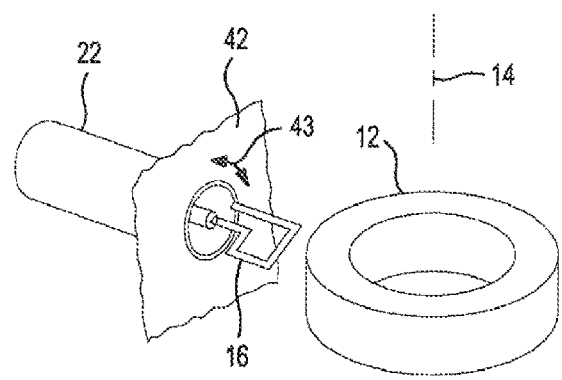
FIG. 11 is a fragmentary view of a loop power coupling system similar to that shown in FIG. 1 for inductively coupling electrical power into the dielectric resonator.

Referring also to FIGS. 2 and 11, in this example, the coupling antenna 16 may be a single loop 20 terminating a coaxial cable 22 leading to the power supply 18 and having an axis 24 generally parallel to axis 14 to couple electrical power inductively between the loop 20 and the dielectric resonator 12 with magnetic flux lines 26 shown in FIG. 1. The single loop 20 may be adjusted as indicated by rotation arrow 43 in FIG. 11 to control the degree of coupling and to provide proper alignment with axis 14. The result is a polarization current flow 27 within the dielectric resonator 12 (shown in FIG. 2) oscillating circumferentially about axis 14 at the resonant frequency of the dielectric resonator 12.

Figure 3:
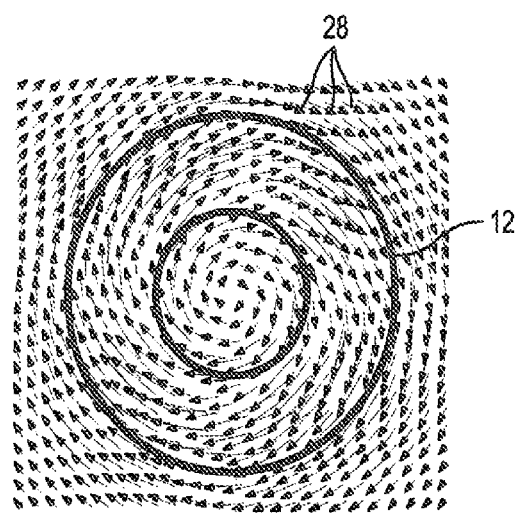
FIG. 3 is a model showing the electrical field in the ring dielectric resonator of FIG. 4 is a perspective view of an alternative embodiment of a ring dielectric resonator having standoffs for thermal conduction path to a supporting structure and airflow.

Referring now to FIG. 3, the electric field 28 within the dielectric resonator 12 at a given instant in time is substantially tangential to the inner and outer circumferential peripheries of the dielectric resonator 12 representing a purely inductive field where parasitic capacitive coupling has been substantially eliminated. The electric field 28 is believed to be of such a high quality because the dielectric resonator is at once its own capacitor and an inductor and therefore electric-potential is exactly zero everywhere inside the dielectric resonator 12 and in the space around the dielectric resonator 12.

Referring again to FIG. 1, a gas source 32, for example, argon for an argon-based plasma may be provided through a regulator 34 to a gas port 36 directing gas along axis 14 through the center of the dielectric resonator 12. Within the dielectric resonator 12, the high electrical fields convert the gas to plasma 40 that may flow along axis 14. The distance of flow is determined by the lifetime of the plasma excitation. Free electrons can always be found in a gas due to naturally occurring background ionizing radiation. When the gas is placed in a region of high intensity electric field the electrons are accelerated and collide with neutral molecules, producing additional electrons by ionization. If the electric field is sufficiently strong, the number of ionizations increases exponentially leading to a process known as electron avalanche and the formation of plasma. In low pressure gas, plasma is principally sustained by the continued acceleration of elections by the electric field and ionizing collisions with the neutrals. In thermal plasma at atmospheric pressure, the flow of current through the plasma heats the gas to very high temperature which also helps to sustain the plasma.

The dielectric resonator 12 may be placed in a radiofrequency shield 42 to reduce power loss due to radiation of electromagnetic energy, minimize human exposure to high intensity nonionizing radiation and control electromagnetic interference. The shield 42 may be connected to the return of the coaxial cable 22.

The use of the dielectric resonator 12 instead of a conductive metallic multi or single loop coil directly driven by an amplifier provides multiple benefits including:

Energy losses in the dielectric resonator 12 are one to two orders of magnitude lower than the conduction losses in a conventional coil. In many applications, this may completely eliminate the need for fluid cooling, greatly reducing the size, cost, and complexity of the plasma source. In semiconductor processing applications, it may be possible to eliminate the need for environmentally damaging dielectric cooling fluids.

The extremely low energy losses in the dielectric resonator 12 translate into a very large electric field strength during the plasma ignition phase, when no power is absorbed by the plasma. This makes for easier and more reliable ignition of the plasma discharge.

The self-resonant nature of a dielectric resonator 12 greatly simplifies or eliminates the need for an external impedance matching network between the dielectric resonator 12 and the power supply 18, thus reducing the size, cost, and the complexity of the plasma source.

The use of ceramic materials, such as alumina, in the dielectric resonator 12 provides a plasma generator compatible with ultra-high-vacuum processes that can be placed directly inside a vacuum chamber in order to improve the coupling to the plasma or to accommodate limited space available for the plasma source.

Creating the dielectric resonator 12 from ceramic materials, such as alumina which have high thermal conductivity, allows for rapid heat removal by conduction. If the dielectric resonator 12 is in direct contact with plasma, this can enable an efficient cooling of the plasma gas, a particularly important feature in gas-discharge laser applications.

The use of ceramic materials, such as alumina for the dielectric resonator maintains good mechanical and electric characteristics at extremely high temperatures in excess of 1,000 degrees Centigrade, which makes a dielectric resonator 12 well suited to applications involving high-temperature atmospheric plasma.

Pure inductive field, extremely low losses, high-temperature operation, and high thermal conductivity, possible with the present design, all enable operation at power levels well in excess of what is possible today with the conventional inductively coupled plasma technology. The maximum power limit will depend on the size of the dielectric resonator, the cooling provided, and the electric breakdown in the RF shield and coupling structures. It is estimated that a 2″ OD ring could operate at 2 kW power level when cooled by natural convection alone, 10 kW with forced air cooling, and 100 kW with water cooling. Much greater power levels may be realised with a large ICR heating antenna which could operate at tens of MW.

Figure 4:
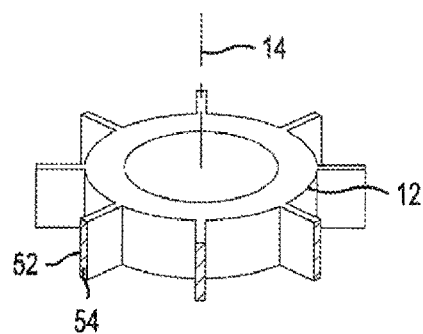

Referring now to FIG. 4, in an alternative configuration dielectric resonator 12 may provide for radially extending standoffs 52 that may, for example, support the dielectric resonator 12 against a supporting structure such as a tubular shield 42 shown in FIG. 1. The ends of the standoffs 54 may be plated with a metal in order to reduce thermal resistance to a metal enclosure to assist in cooling of the dielectric resonator 12 which may also be cooled by natural convection or forced flow of air around the standoffs 52.

Figure 5:
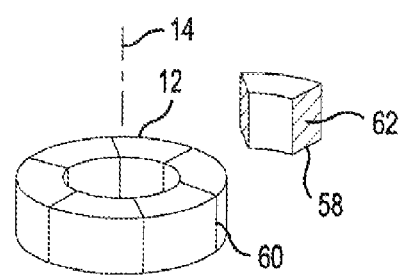
FIG. 5 is a perspective view of a ring dielectric resonator fabricated of individual sectors and showing one such sector.

Referring now to FIG. 5, particularly for larger dielectric resonators 12, the dielectric resonator 12 may be assembled from multiple annular sectors 58 placed together at seams 60 being an abutment of metal plated end surfaces 62. The small amount of non-dielectric material does not significantly impact the benefits of the dielectric.

Figure 6:
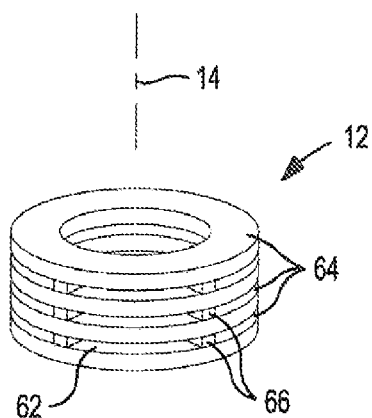
FIG. 6 is a perspective view of a dielectric resonator fabricated from multiple laminated rings.

Referring now to FIG. 6, the dielectric resonator 12 may be constructed out of multiple thin rings 64 aligned along common axis 14 held apart by thin insulating spacers.

Smaller rings may be easier to manufacture and transport and the gaps between the end surfaces 62 may provide improved cooling while preventing undesirable flow of dielectric polarization currents in the axial direction.

Figure 7:
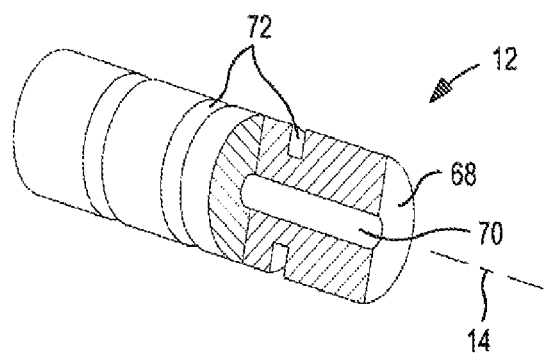
FIG. 7 is a perspective partial cutaway view of a dielectric resonator fabricated from a rod having circumferential grooves and a central axial bore.

Referring now to FIG. 7, a similar result may be achieved by fabricating the dielectric resonator 12 in the form of an elongated tube 68 having a central axial bore 70 and outer circumferential notches 72 serving to prevent axial polarization currents.

Figure 8:
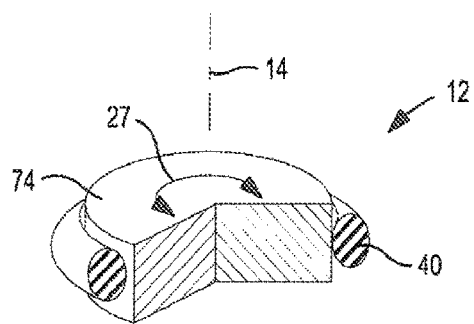
FIG. 8 is a perspective partial cutaway view of a disk dielectric resonator showing an external plasma region.

Referring now to FIG. 8, it will be appreciated that the dielectric resonator 12 need not be a ring but that a toroidal plasma 40 may be generated around the outer periphery of a dielectric resonator 12 in the form of a disk 74. The toroid of the plasma 40 may be centered about axis 14 being an axis of symmetry of the disk 74. Proper selection of the resonant mode ensures a primary circumferential current component 27 in the resonance of the disk 74.

Figure 9:
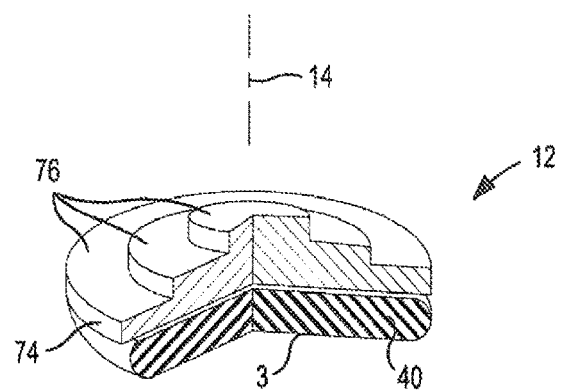
FIG. 9 is a perspective partial cutaway view of a disk dielectric resonator providing a stepped surface disk to produce an axial disk-shaped plasma.

Referring now to FIG. 9, by establishing a series of circular steps 76 of increasing height as one moves toward the center of the disk 74, the plasma 40 may be displaced to an opposite face of the disk 74 of the dielectric resonator 12. The idea behind the steps 76 is to address the fact that in a simple ring or disk, the electric field is zero on the axis and increases nearly linearly towards the outer radius. The field and the plasma are most intense near the ring. The steps serve to increase the polarization current at smaller radii (by increasing the total thickness of the ring) so that the induced electric field is more uniform between the axis and the outer radius. It is believed that this may improve radial plasma uniformity. As far as displacing the plasma is concerned, plasma on the other side of the disk would have to be suppressed by high-vacuum or higher gas pressure, for example.

Figure 10:
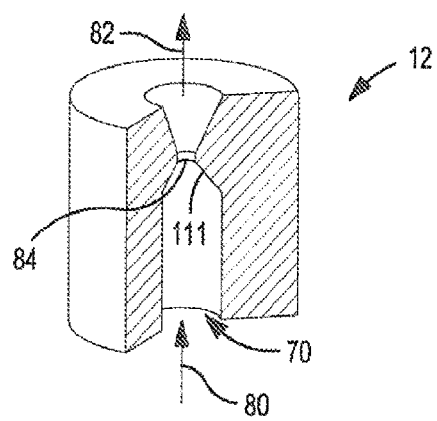
FIG. 10 is a perspective partial cutaway view of a nozzle for use in plasma cutting and welding or plasma thrusters.

Referring now to FIG. 10, in one embodiment the dielectric resonator 12 may provide for a convergent-divergent nozzle 111 for the purpose of accelerating hot subsonic plasma flow 80 into supersonic plasma flow 82, in applications such as plasma cutting and welding or rocket engines. In this case, the dielectric resonator 12 includes a central bore 70 that necks inward to a smaller diameter 84, for example, to produce a de Laval nozzle downstream from the point of plasma generation.

It will be appreciated that that many variants shown in the above Figs. may be combined in various ways. For example, the standoffs 52 of FIG. 4 can be combined with the rocket nozzle of FIG. 10 in order to facilitate heat removal, or the notches 72 shown in FIG. 7 can be implemented in the disks of FIGS. 8 and 9, in the form of circumferential grooves cut downward into one of the faces of the disk 74 to promote the desired current flow patterns.

Figure 12:
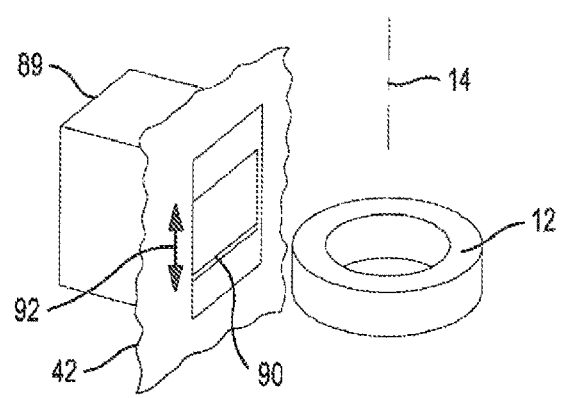
FIG. 12 is a figure similar to FIG. 11 showing a coupling system employing a microwave waveguide.

Referring now to FIG. 12, other methods of exciting the dielectric resonator 12 into resonance may be employed, for example, placing the dielectric resonator 12 at the end of a waveguide 89 directed generally perpendicular to the axis 14 driven by a microwave source. An opening 90 of the waveguide 89 may be controlled by an iris mechanism that may open and close a pair of irises 94 as indicated by arrows 92 to control the degree of coupling between the microwave source and the dielectric resonator 12.

The present invention may be used in an optical emission spectrometer (OES) where their purpose is to excite the atomic and molecular species in an unknown chemical sample and produce light. The spectroscopic analysis of the light emitted by the plasma is used to determine the type and quantity of the chemical substance present in the sample. The present invention may also be used in a mass spectrometer (MS) where the purpose is to create ions of a sample material introduced into the plasma. The ions are extracted from the plasma and are transported into a vacuum system and are mass analysed. Plasma properties critically affect the analytical performance of an OES, in terms of the ability to process samples in aqueous or organic solvents without extinguishing the plasma, the ability to operate on different plasma gases for improved safety and economy, the ability to detect different kinds of chemicals, the ability to accurately measure a very large range of analyte concentrations, the ability to detect extremely small concentrations of the analyte, the ability to process many samples in a short amount of time the ability to produce stable results when measurements are repeated over a long period of time, etc. Plasma properties critically affect the analytical performance of a MS in a similar way as they affect the performance of an optical-emission spectrometer. Unique to MS, the ions created in an atmospheric pressure plasma must be transferred to a high-vacuum environment of the mass-spectrometer through the, so called, interface part of the MS. The interface contains multiple metallic cones with small orifices which separate the regions of different pressure. The cone whose one side is in direct contact with atmospheric pressure plasma is known as the sampler cone. The performance of the sampler cone is most critically affected by the parasitic capacitive coupling of a conventional RE coil, leading to reduced ion transmission, arcing, and erosion of the cone. Most commonly used inductively coupled plasma sources for MS operate at radiofrequencies up to 40 MHz.

The plasma source may also be used as an atomisation source for atomic absorption (AA) spectroscopy.

Typical plasma sources for this application may operate at radio-frequencies up above 40 MHz with much higher frequencies implemented by this design (i.e. the present invention). Alternatively, the design may provide plasma at microwave frequencies, such as 915 MHz or 2,450 MHz, using a magnetron device as a source of large amount of microwave power.

Existing designs for microwave plasma generators are dominated by capacitive coupling or retain a significant amount of parasitic capacitive coupling, which has a serious negative impact on the plasma source, or have form factors that would require significant modifications to the conventional mechanical, optical, and chemical interface to the rest of the spectrometer, an interface which has proven itself over many years of operation of radio-frequency CUES in the field (i.e. as proven with ICP plasma generation systems). The parasitic capacitive coupling present in prior art microwave plasma generators such as Surfatron, Beenakker cavity, Okamoto cavity, Surfaguide, Multi-helix torch, TIA torch, etc. has a serious negative impact on the performance of an inductive plasma source leading to: a) plasma non-uniformities, b) poor control over ion speeds and trajectories, c) deposition or sputtering of the walls of the plasma chamber, d) power dissipation in non-essential plasma processes, and e) limitation on the amount of electrical power that can be efficiently coupled into useful plasma processes.

In contrast, the plasma source of the present design may extend the operation of the conventional radio-frequency inductively coupled plasma sources to microwave frequencies, practically eliminating parasitic capacitive coupling which has limited previous designs, while requiring minimum modifications to the established mechanical, optical, and chemical interface with the rest of the spectrometer. In addition, the extremely low losses of the novel field applicator, allow for a complete elimination of the fluid cooling system, thus reducing the size, cost, and the complexity of the spectrometer and improving reliability. The plasma source of the present design also allows a range of different plasma gases to be used including gases comprising nitrogen or air. In one preferred embodiment the plasma is sustained in air. In another preferred embodiment the plasma is sustained in nitrogen.

Figure 15:
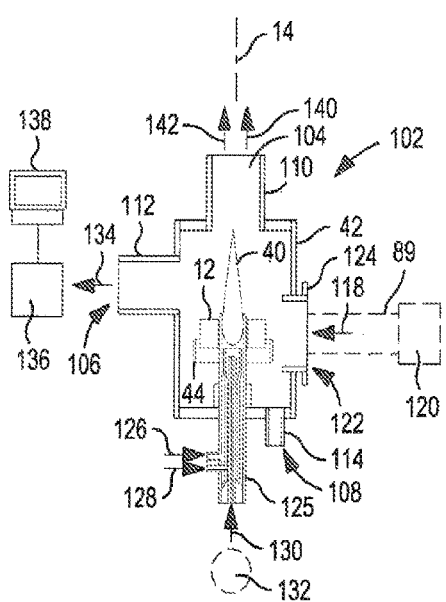
FIG. 15 is a simplified cross-sectional view of a spectrometer incorporating the dielectric resonator of the present invention.

Referring now to FIG. 15 a microwave inductively coupled plasma source for optical-emission spectroscopy 102, which uses a dielectric resonator 12 of the present invention, made out of high-density Alumina ($Al_2O_3$) ceramics in the form of a circular annulus. The dielectric resonator 12 may be supported within cylindrical radio-frequency shield 42 made of metal, such as aluminum, and has several circular openings 104, 106, and 108 each surrounded with aluminum tubular extensions 110, 112, and 114 respectively. The tubular extensions 110-114, are designed to have a sufficiently small diameter and sufficiently long length to form cylindrical waveguides below cutoff, greatly attenuating the propagation of microwaves through the extension tubes, as is well understood in the microwave art, in order to minimize the leakage of microwave energy outside of the shield 42.

Microwave power 118 from waveguide 89 communicating with magnetron 120 is provided at a frequency of 2,450 MHz an d applied to the dielectric resonator 12 through a rectangular opening 122 in the shield 42 by the means of a coupler 124. The resonant frequency of the dielectric resonator 12 can be finely adjusted by varying the axial location of the tuning element 44, made in the form of an aluminum ring, positioned coaxially with the ring of dielectric resonator 12.

A triaxial manifold 125 is directed along the axis 14 centered within opening 104 and aligned with inner diameter of dielectric resonator 12 and made out of quartz or alumina tubing. The triaxial manifold is in the form of a conventional torch which may be similar to that used with inductively coupled plasmas. A plasma cooling gas 126 is applied to an outer ring of the triaxial manifold 125 while a plasma auxiliary gas 128 is applied to the next inner ring and the center bore receives the dissolved analytical sample or solid particles of sample 130 from a sample source 132 to be analyzed. The sample 130 is in the form of an aerosol, or discrete particles, entrained in a gas, that may be directly introduced into the plasma 40.

Light 134 emitted from the plasma 40 in a direction radial to axis 14 passes through the tubular extension 112 for analysis by a light sensor 136 coupled to an analyzing computer 138 that may determine frequency components of the light 134 according to methods known in the art. Alternatively or in parallel, for the purposes of the, so called, axial OES, light 140, emitted by the plasma 40 in the axial direction of axis 14, is transferred through the tubular extension 110 for further spectroscopic analysis by a similar light sensor 136 (not shown for clarity). The tubular extension 110 also directs the hot plasma gases and chemical products 142 to an exhaust venting system (not shown.) The opening 108 and the tubular extension 114 allow for air cooling of the plasma generator 12 by natural convection or by forced flow of air.

The optical emission spectrometer of the present invention preferably comprises a plasma generator, the plasma generator comprising a dielectric resonator, a dispersive element for dispersing light emitted by the plasma according to the wavelength of the light, and an optical detector for detecting the dispersed light.

Figure 16:
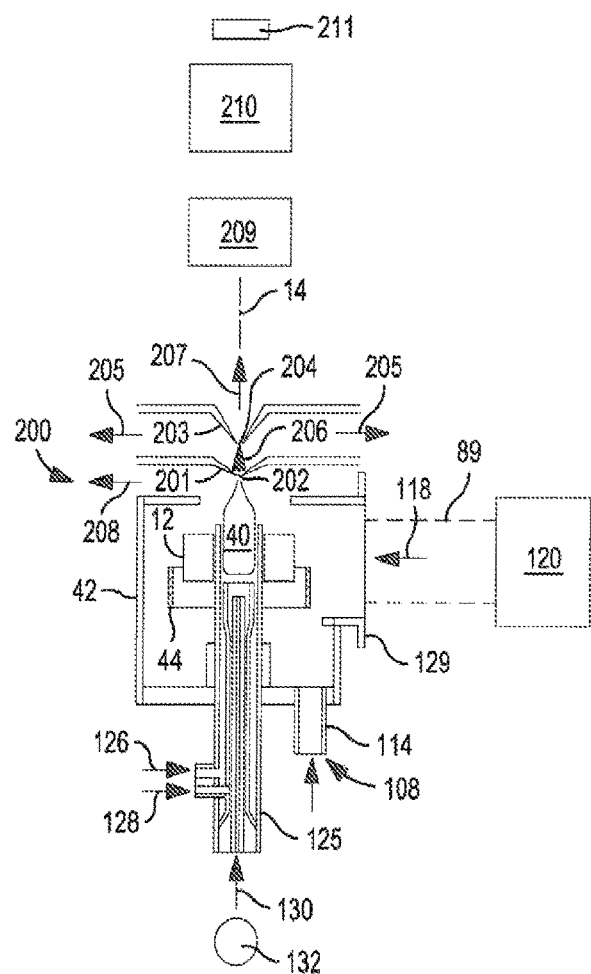
FIG. 16 is a simplified schematic cross-sectional view of a mass spectrometer incorporating the dielectric resonator of the present invention.

FIG. 16 is a simplified schematic cross-sectional view of a mass spectrometer incorporating the dielectric resonator of the present invention. Most commonly used inductively coupled plasma sources for MS operate at radiofrequencies up to 40 MHz. Several designs have been proposed and tested with a goal of extending the operation of the plasma sources for MS to microwave frequencies, such as 915 MHz or 2,450 MHz, where a magnetron device could serve as an efficient source of large amount of microwave power. The existing analytical results indicate that microwave excited plasma offers unique advantages that complement the analytical power of a radio-frequency based plasma sources. However, one of the key obstacles in the ability to produce a high quality analytical plasma at microwave frequencies has been the lack of a field applicator capable of producing a pure inductive coupling to the plasma. All of the designs proposed to date are either dominated by capacitive coupling or retain a significant amount of parasitic capacitive coupling, which has a serious negative impact on the plasma source performance as previously outlined. In addition, all of the previous designs require significant modifications to the conventional mechanical, optical, and chemical interface to the rest of the spectrometer, an interface which has proven itself over many years of operation of radio-frequency MS in the field.

In contrast, the plasma source for MS, based on the field applicator according to the present invention, extends the operation of the conventional radio-frequency inductively coupled plasma sources to microwave frequencies, practically eliminating parasitic capacitive coupling which has limited previous designs, while requiring minimum modifications to the established mechanical, ion, and chemical interface with the rest of the spectrometer. In addition, the extremely low losses of the novel field applicator, allow for a complete elimination of the fluid cooling system, thus reducing the size, cost, and the complexity of the spectrometer.

FIG. 16 shows a schematic simplified cross-section of a microwave inductively coupled plasma source for mass spectrometry 200, which uses a field applicator 12 of the present invention, made out of high-density Alumina ($Al_2O_3$) ceramic in the form of a ring. The microwave inductively coupled plasma source for MS 200 has many components in common with the microwave inductively coupled plasma source for OES 102 shown in FIG. 15, and like components have the same identifiers. Additional components shown in FIG. 16 will now be described. The sampler cone 201 has a small orifice 202 and the skimmer cone 203 has a small orifice 204. The region between the sample cone 201 and the skimmer cone 203 is maintained at a low pressure by exhausting the gas 205 by means of a vacuum pump (not shown). The ionized sample 206 enters the low pressure region between the sample and skimmer cones through the orifice 202. Ions 207 are further transmitted through the orifice 204 into the high-vacuum region of the mass-spectrometer. The mass spectrometer comprises ion focusing components 209 which comprise at least one ion focusing element, a mass analyser 210 and an ion detector 211. There may be two or more stages of pumping (not shown) disposed within the mass spectrometer. The mass spectrometer is controlled by a controller (not shown), which is preferably a computer. Detected signal from ion detector 211 is recorded, preferably also using a computer, which may be the same computer as is used as the controller. The heated plasma gas 208 which has not penetrated the orifice 202 is exhausted through the annular region between the RE shield 42 and the sample cone 201.

Preferably the optical emission spectrometer or the mass spectrometer comprises a plasma generator according to the present invention wherein the radiofrequency power source provides between 0.5 and 2 kW of power into the plasma.

The performance of an optical emission spectrometer according to the present invention was compared with that of a conventional ICP optical emission spectrometer operating in radial viewing mode. A conventional ICP torch was located within the central aperture of the dielectric field applicator, the torch being connected to the gas supplies of the spectrometer. The dielectric field applicator and torch were mounted such that the plasma formed within the central aperture of the dielectric field applicator was aligned for viewing by a high-resolution Echelle spectrometer in radial viewing mode. Advantageously the plasma generator was operated with both air and nitrogen without any change to the plasma generator system due to the unique way in which the ceramic ring works as both an inductor and a tuning device and because the electrical coupling into the plasma is substantially purely inductive with negligible capacitive coupling.

Figure 17:
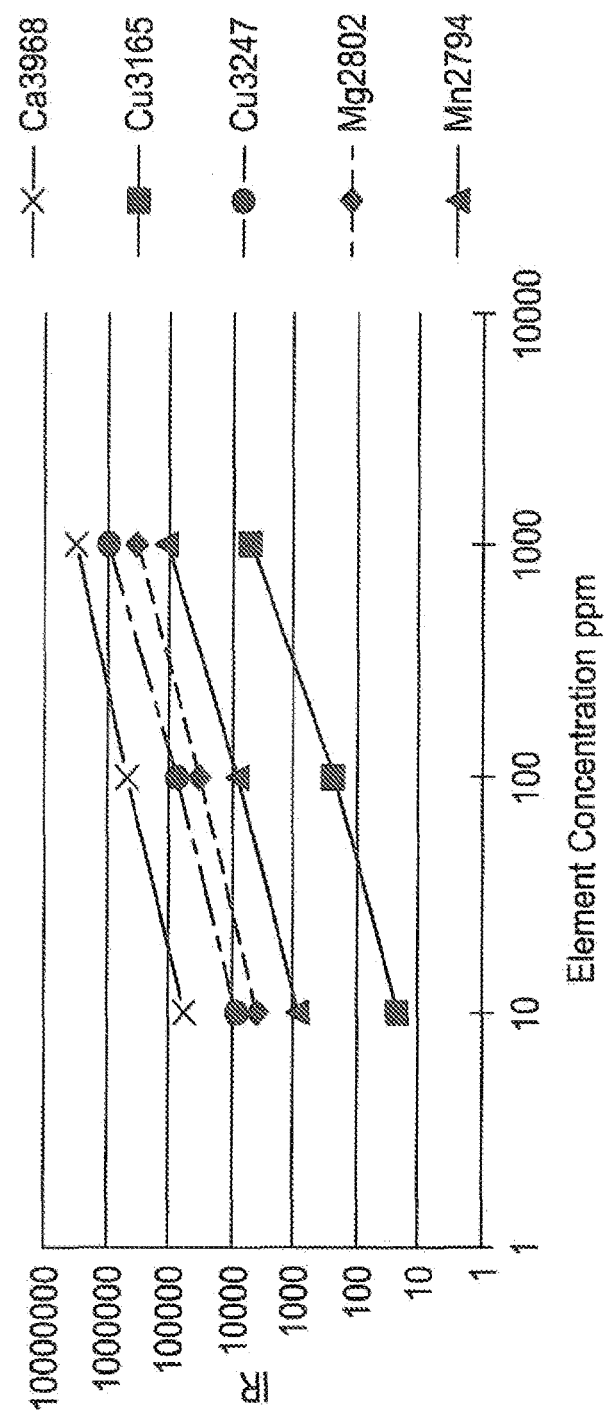
FIG. 17 shows a plot of signal intensity in counts per second (IR) vs. element concentration for a range of elements present in a test solution as measured by an optical emission spectrometer of the present invention.

FIG. 17 shows a plot of signal intensity in counts per second (IR) vs. element concentration for a range of elements utilizing a range of hard and soft lines measured using an optical emission spectrometer of the present invention. The energy sums for the five lines are:

Ca3968, 9.23 eV (3.12 eV energy of excitation and 6.11 eV energy of ionization);
Cu2165, 5.73 eV (excitation energy);
Cu3247, 3.82 eV (excitation energy);
Mg2802, 12.07 eV (4.42 eV energy of excitation and 7.65 eV energy of ionization);
Mn2794, 12.25 eV (4.82 eV energy of excitation and 7.42 eV energy of ionization).

Figure 18:
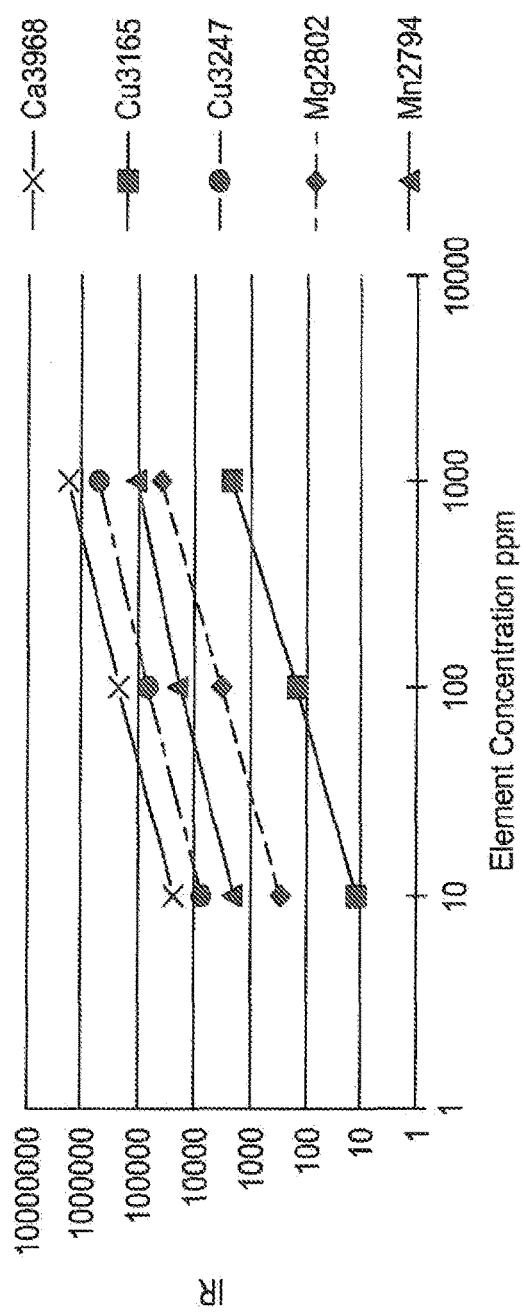
FIG. 18 shows a plot of signal intensity in counts per second (IR) vs. element concentration for a range of elements present in a test solution which also contained 3% salt matrix, as measured by an optical emission spectrometer of the present invention.
Figures 19A, 19B:
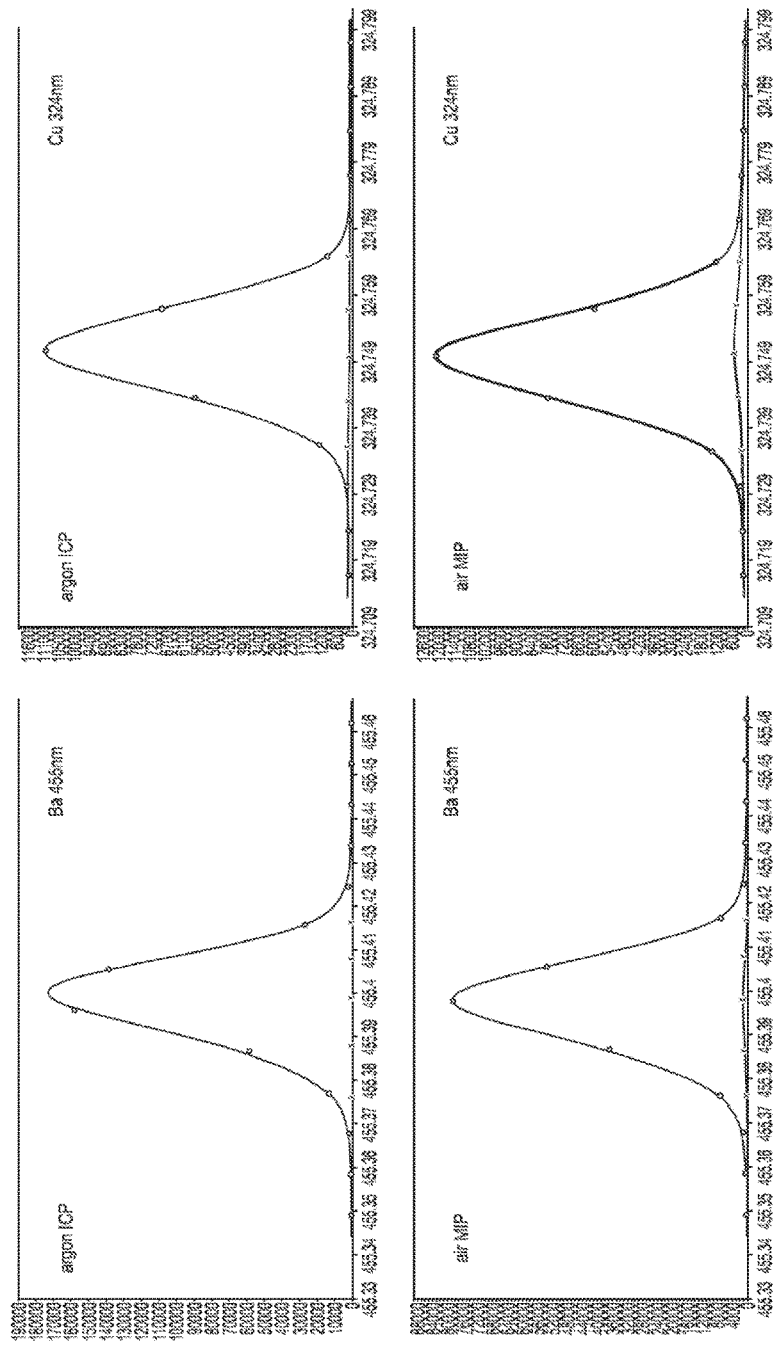
FIGS. 19(a) to (d) are peak profile plots showing measured peak intensities from a multielement standard and baselines winch are background signals from measured blanks (deionised water), for a conventional argon ICP source and the plasma source of the present invention operating with air.
Figures 19C, 19D:
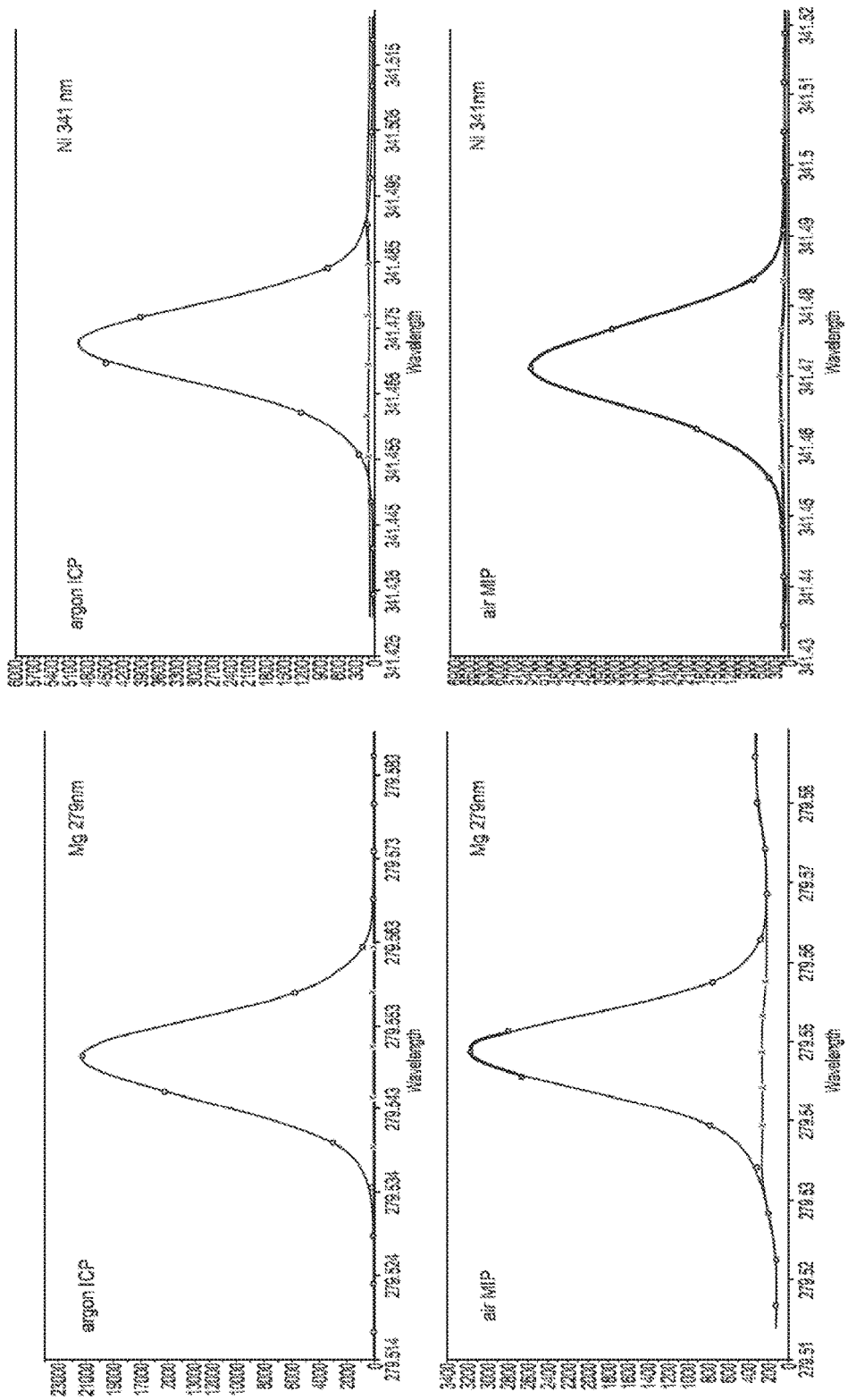

Linearity was also examined for a solution containing 3% salt matrix. The results obtained are shown in FIG. 18 which indicates that linearity is maintained despite the presence of a large concentration of sodium from the salt, which being more easily ionized can modify the distribution of detected ionic and atomic lines and line emission levels.

FIG. 19(a) to (d) are peak profile plots showing measured peak intensities from a multielement standard and baselines which are background signals from measured blanks (deionised water), for a conventional argon ICP source and the plasma source of the present invention operating with air. The multi element standard contained 0.2 ppm Ba and Mg, 1 ppm Cu, 5 ppm Ni. Cu and Ni are soft atom lines and give much the same performance with conventional argon ICP and the air plasma source of the present invention. Ba is a harder ion line and performs better in the conventional argon ICP plasma, but the peak intensity in the air plasma is only a little less than half that in the argon ICP plasma. Other forms of dielectric resonator are contemplated, two examples of which are presented in FIGS. 20 and 21.

Figure 20:
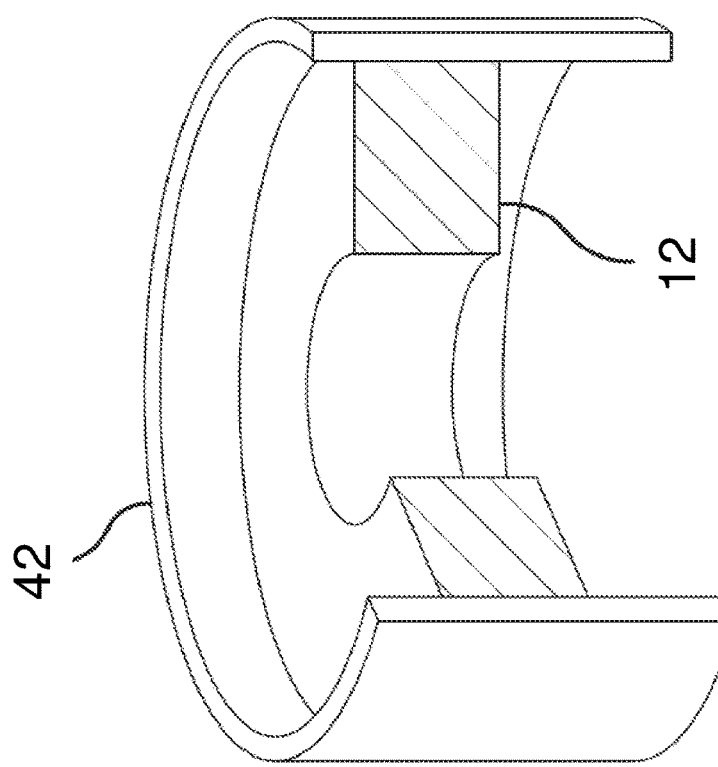
FIG. 20 is a perspective partial cutaway view of a dielectric resonator together with an RF shield in direct contact with an outer surface of the dielectric resonator.
Figure 22A:
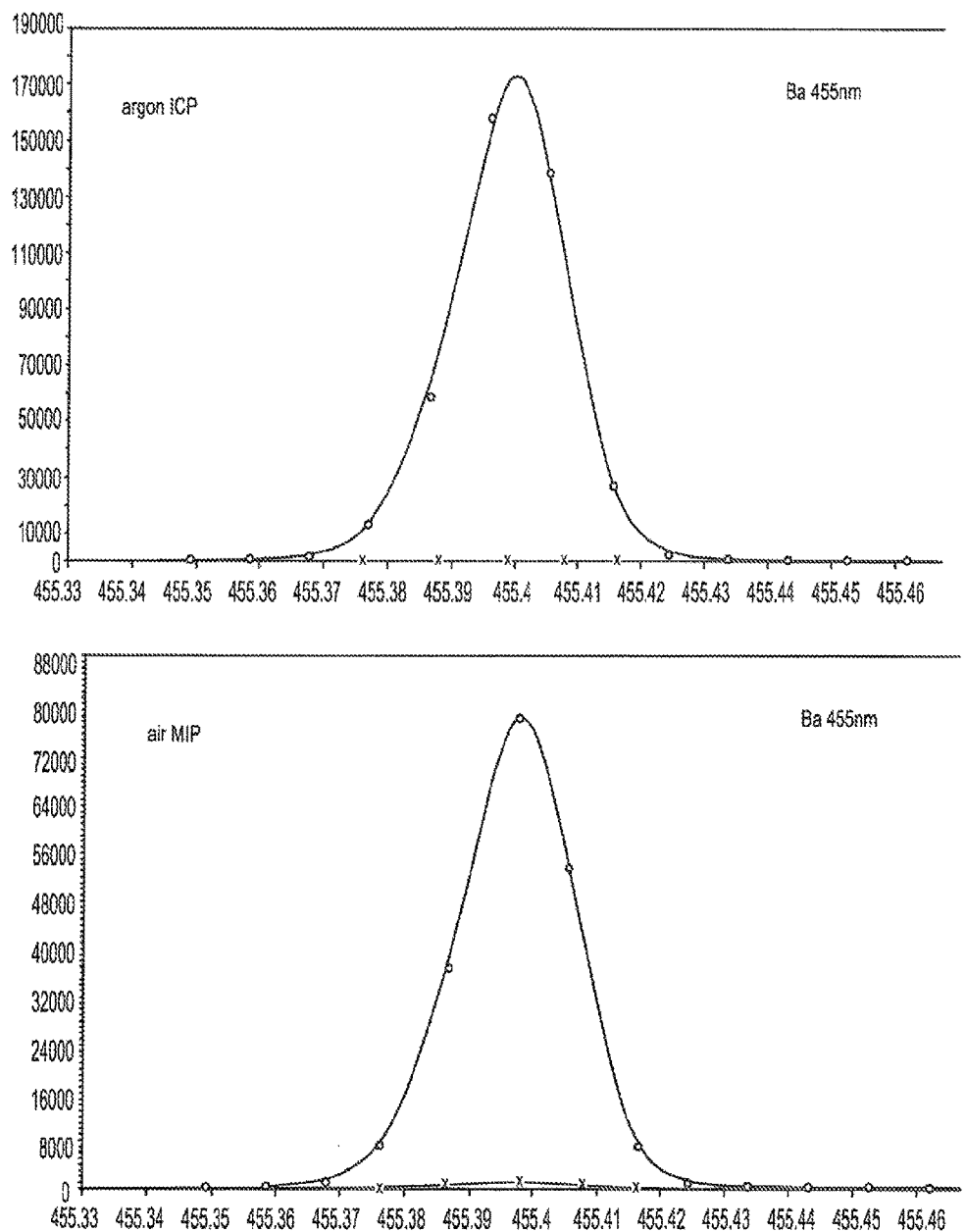
Figure 22B:
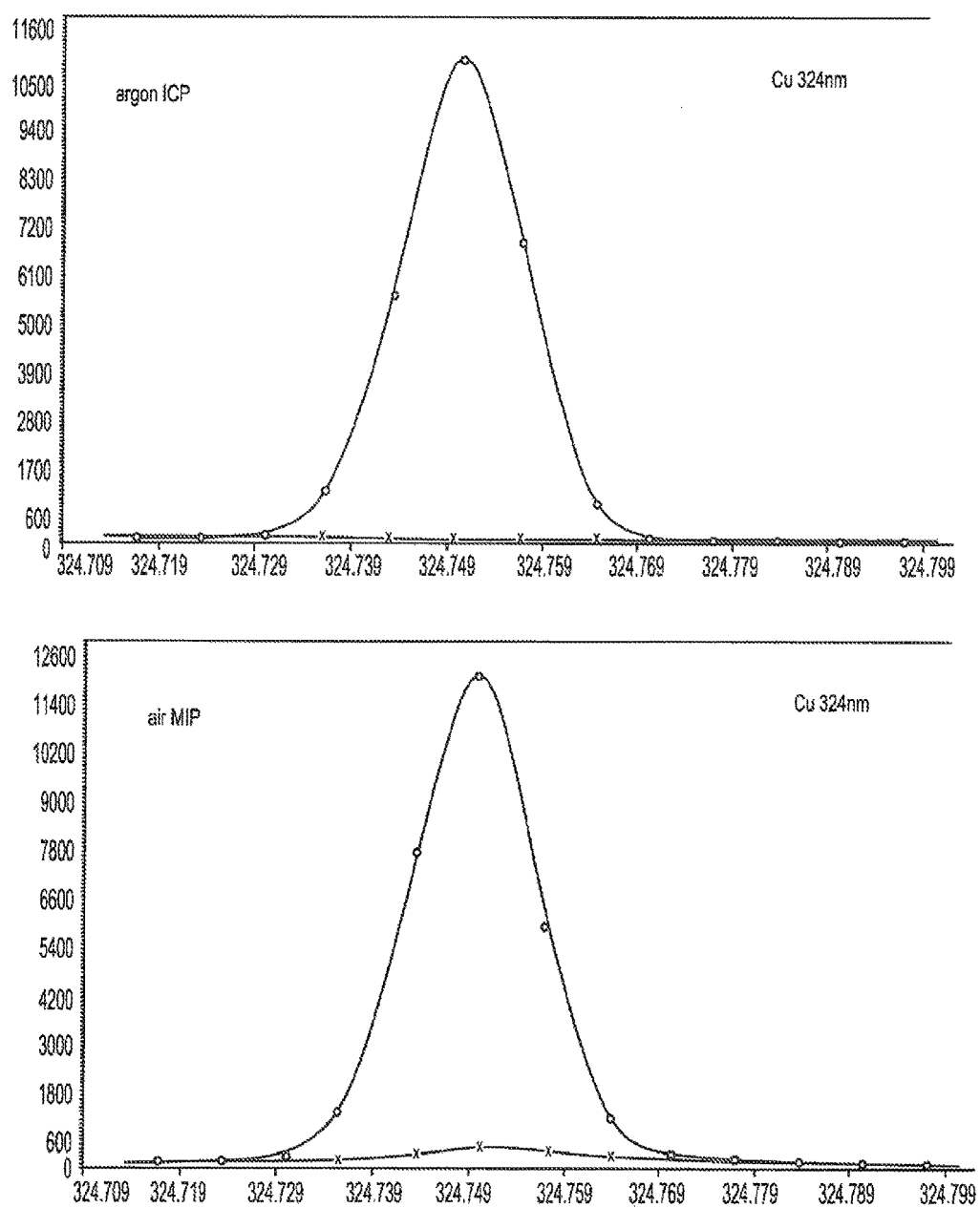
Figure 22C:
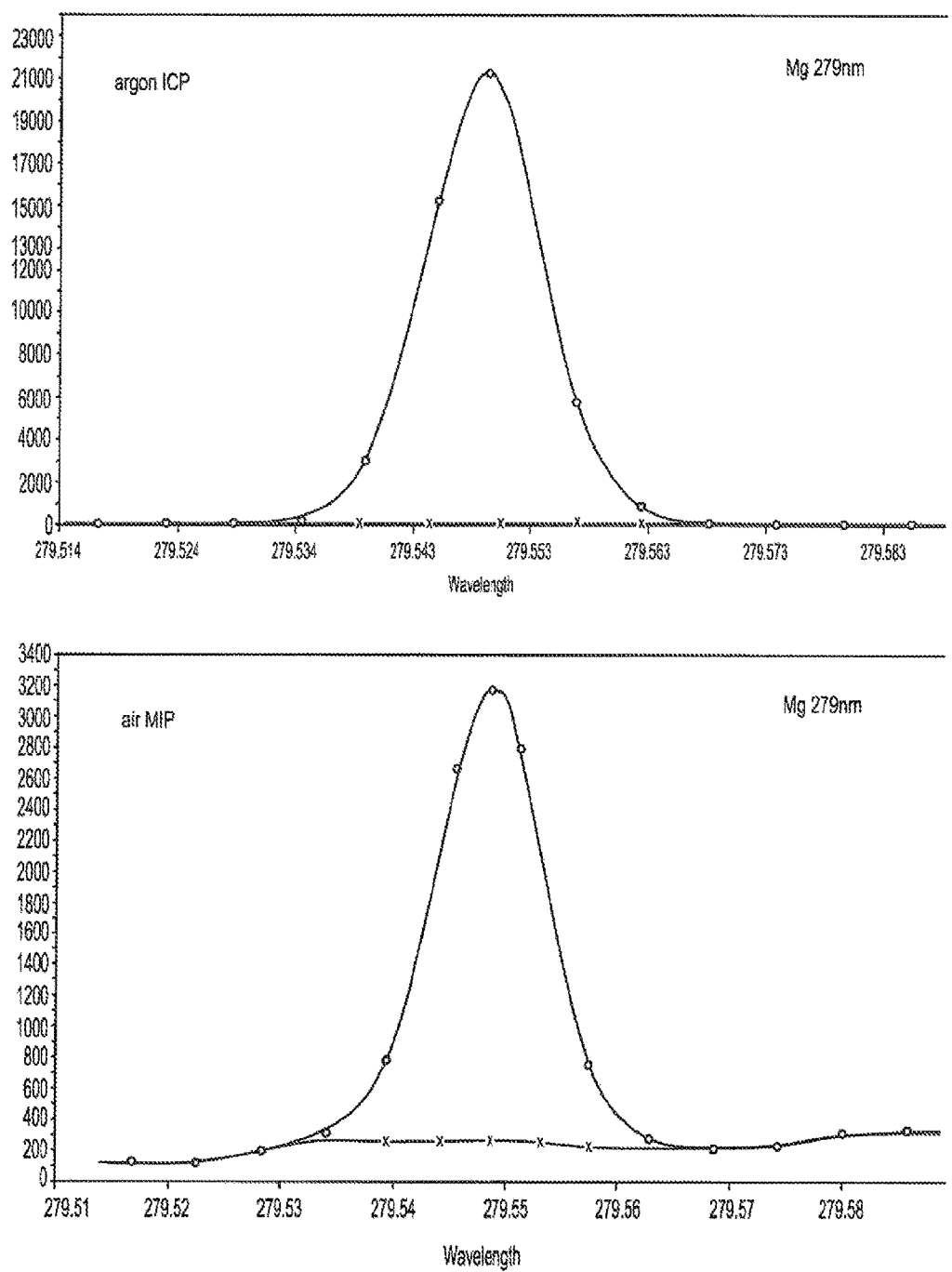
Figure 22D:
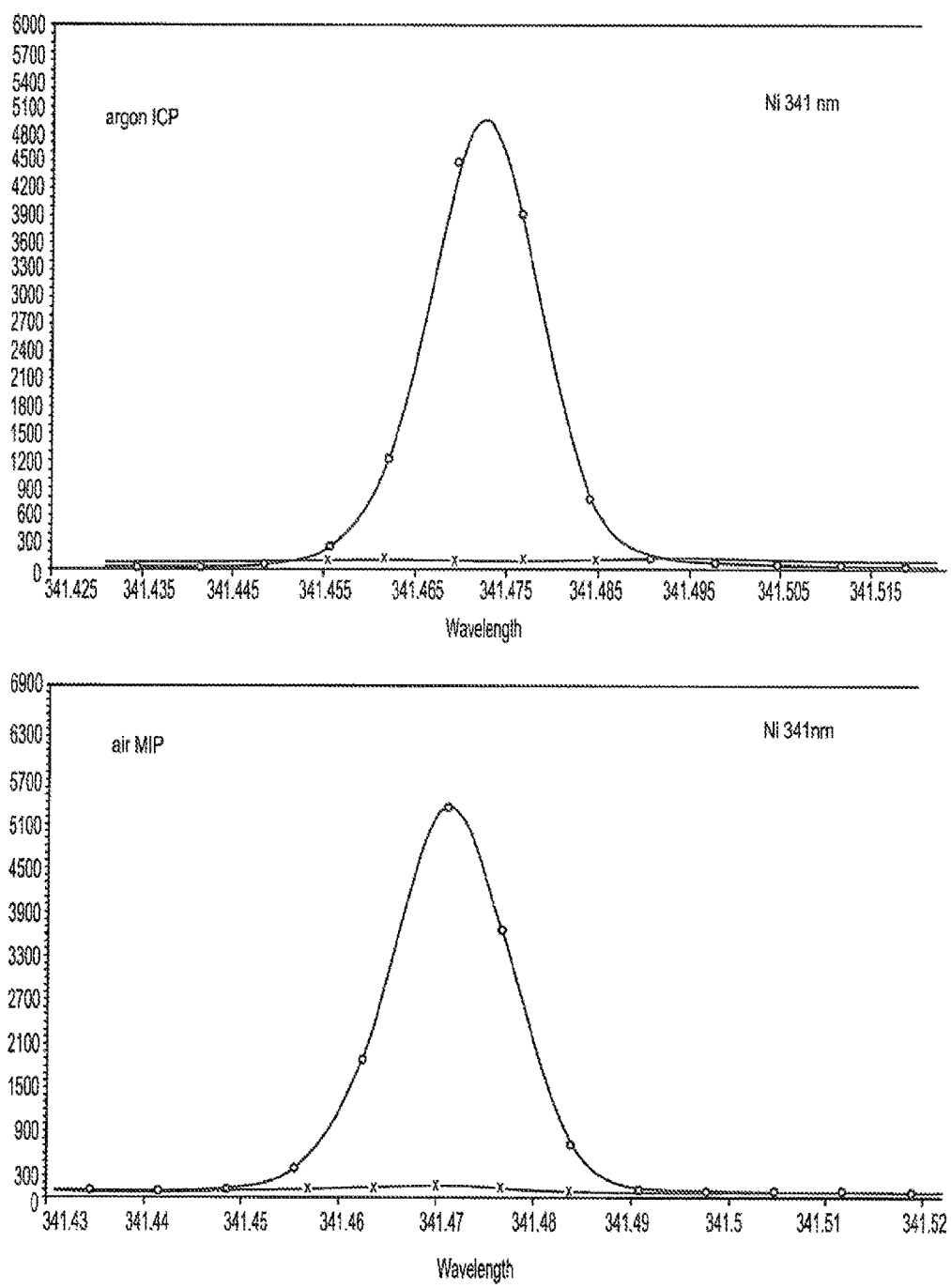
Figure 23:
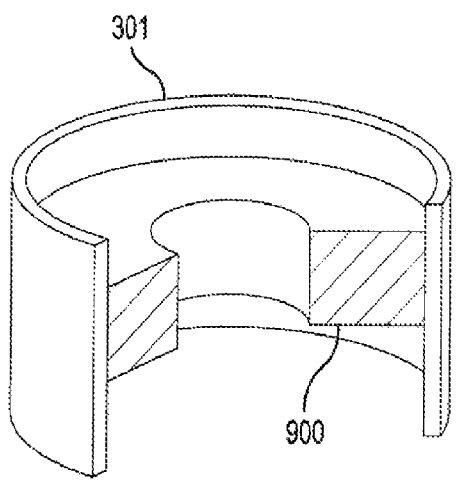
Figure 24:
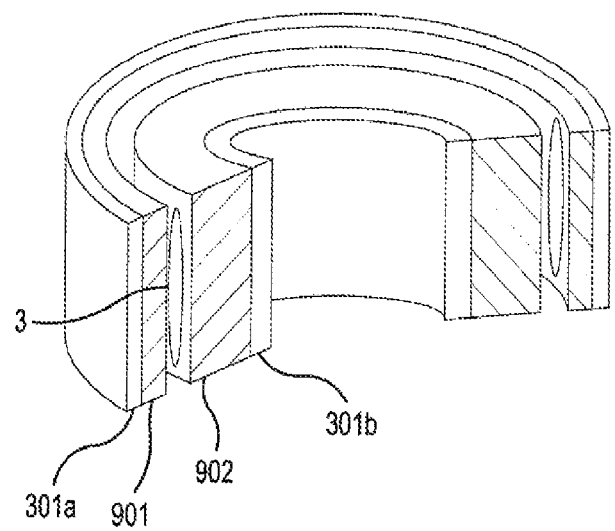

FIG. 20 is a perspective partial cutaway view of a dielectric resonator which is in the form of a ceramic ring 12 together with an RF shield 42 in direct contact with an outer surface of the dielectric resonator 12. This configuration offers the advantage of smaller size and better transfer of heat to the RF shield 42. The surface of the ceramic ring 12 which is in contact with the RF shield 42 may be plated with metal.

FIG. 21 is a perspective partial cutaway view of a dielectric resonator in the form of two coaxial ceramic rings 12c and 12d, together with two concentric RF shields. The outer surface of the larger ring 12c is in direct contact with outer RF shield 42aa. The inner surface of the smaller ring 12d is in direct contact with inner RF shield 42b. The plasma 40 may be formed in the annular gap between the rings 12c and 12d.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

The term "ring" should be understood to generally mean a topological surface of genius one and not require nor exclude, for example, a circular profile, radial symmetry or particular aspect ratios of with a diameter to height except as explicitly noted.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications are hereby incorporated herein by reference in their entireties.

We claim:

1. A spectrometer comprising a plasma generator, the plasma generator comprising:
   a dielectric resonator structure of dielectric material extending around a central axis;
   a port for introducing gas and a material to be studied into a region adjacent the dielectric resonator structure; and
   a radiofrequency power source electrically coupled to the dielectric resonator structure to promote an alternating polarization current flow at a natural resonant frequency of the dielectric resonator structure and directed circumferentially about the central axis along a continuous circular path within the dielectric material of the dielectric resonator to generate plasma in the gas to interact with the material to be studied.

2. The spectrometer of claim 1 wherein the radiofrequency power source is electromagnetically coupled to the dielectric resonator structure.

3. The spectrometer of claim 2 wherein axial surfaces of the dielectric resonator are substantially free from electrical shielding.

4. The spectrometer of claim 1 wherein the dielectric resonator structure is electrically coupled to the plasma substantially only by induction, there being negligible capacitive coupling.

5. The spectrometer of claim 1 wherein the dielectric resonator has a quality factor of greater than 100.

6. The spectrometer of claim 1 wherein the dielectric resonator has electrical resistivity greater than $1 \times 10^{10}$ Ω·cm.

7. The spectrometer of claim 1 of wherein the dielectric resonator has a melting point greater than a melting point of copper.

8. The spectrometer of claim 1 wherein dielectric resonator has a dielectric constant with a loss tangent of less than 0.01.

9. The spectrometer of claim 1 wherein the dielectric resonator has a dielectric constant of greater than five.

10. The spectrometer of claim 1 wherein a dielectric material of the dielectric resonator is selected from the group consisting of alumina ($Al_2O_3$) and calcium titanate ($CaTiO_3$).

11. The spectrometer of claim 1 wherein the gas is selected from the group consisting of nitrogen and air.

12. The spectrometer of claim 1 wherein the dielectric resonator is selected from the group consisting of a ring and a cylindrical annulus having a central opening along the axis.

13. The spectrometer of claim 12 wherein dielectric resonator has a central opening of at least one millimeter in diameter.

14. The spectrometer of claim 12 wherein the dielectric resonator has a central opening which is circular and has a diameter of between 15 mm and 25 mm.

15. The spectrometer of claim 12 wherein the port further includes a gas port introducing gas into the ring along an axis of the dielectric resonator.

16. The spectrometer of claim 12 wherein dielectric resonator has a central opening of at least one half inch (0.0127 m) in diameter.

17. The spectrometer of claim 1 wherein the radiofrequency power source is driven at a frequency which is within two full width at half maximum (FWHM) bandwidths of the resonant frequency of the dielectric resonator structure when the resonator is loaded.

18. The spectrometer of claim 1 wherein the radiofrequency power source automatically seeks the natural resonant frequency of the dielectric resonator structure to output radiofrequency power substantially at the natural resonant frequency of the dielectric resonator structure.

19. The spectrometer of claim 1 wherein the radiofrequency power source is selected from the group consisting of one or more of a magnetron, a solid state oscillator and a vacuum tube oscillator.

20. The spectrometer of claim 1 wherein the radiofrequency power source output frequency lies within a range from 20 to 1000 MegaHertz.

21. The spectrometer of claim 1 wherein the radiofrequency power source output frequency lies within a range selected from the group consisting of: 1 MHz-10 GHz, 30 MHz-300 MHz, and 300 MHz-3 GHz.

22. The spectrometer of claim 1 wherein the approximate radiofrequency power source output frequency is selected from the group consisting of 27 MHz, 60 MHz, 430 MHz, 915 MHz, 2450 MHz.

23. The spectrometer of claim 1 wherein the radiofrequency power source provides between 0.5 and 2 kW of power into the plasma.

24. The spectrometer of claim 1 further comprising:
   an optical sensor for measuring frequency of light emitted by the material when heated by the plasma.

25. The spectrometer of claim 24 wherein the optical sensor comprises a dispersive element for dispersing light emitted by the plasma according to the wavelength of the light; and an optical detector for detecting the dispersed light.

26. The spectrometer of claim 25 wherein the dispersive element comprises a grating.

27. The spectrometer of claim 25 further including elements selected from the group consisting of one or more of: one or more optical focusing elements; mirrors for changing the direction of one or more beams of light; a focal plane array detector comprising multiple detecting elements for simultaneously detecting light dispersed by the dispersive element, the focal plane array detector forming at least part of the optical detector, a controller for controlling the spectrometer, and a controller for receiving an output from the optical detector.

28. The spectrometer of claim 1 further comprising:
   a manifold comprising a gas port suitable for delivering sample material into the plasma generated by the plasma generator;
   a sample cone and a skimmer cone;
   at least one ion focusing element;
   a mass analyzing element; and
   an ion detector for detecting sample material ionized by the plasma.

29. The spectrometer of claim 28 further comprising a controller for controlling the spectrometer and a controller for receiving an output from the ion detector.

30. The spectrometer of claim 1 selected from the group consisting of an optical emission spectrometer and a mass spectrometer.

31. The spectrometer of claim 1 wherein the dielectric resonator and the radiofrequency power source are placed within a waveguide and the radiofrequency power source is electrically coupled to the dielectric resonator structure by radiation through the waveguide.

* * * * *